United States Patent
Gowda et al.

(10) Patent No.: US 11,678,838 B2
(45) Date of Patent: *Jun. 20, 2023

(54) AUTOMATED DETECTION OF BREATHING DISTURBANCES

(71) Applicant: Fitbit, Inc., San Francisco, CA (US)

(72) Inventors: Suraj Gowda, Berkeley, CA (US); Conor Joseph Heneghan, Campbell, CA (US); Shelten Gee Jao Yuen, Berkeley, CA (US); Anjian Wu, San Francisco, CA (US); Daniel Joel Freschl, Berkeley, CA (US); Peter W. Richards, San Francisco, CA (US); Chris H. Sarantos, San Francisco, CA (US); Jonathan Wonwook Kim, Emeryville, CA (US)

(73) Assignee: FITBIT, INC., San Francisco, CA (US)

( * ) Notice: Subject to any disclaimer, the term of this patent is extended or adjusted under 35 U.S.C. 154(b) by 159 days.

This patent is subject to a terminal disclaimer.

(21) Appl. No.: 17/136,355

(22) Filed: Dec. 29, 2020

(65) Prior Publication Data

US 2021/0161464 A1  Jun. 3, 2021

Related U.S. Application Data

(63) Continuation of application No. 16/428,412, filed on May 31, 2019, now Pat. No. 10,874,345, which is a (Continued)

(51) Int. Cl.
*A61B 5/00* (2006.01)
*A61B 5/0205* (2006.01)
(Continued)

(52) U.S. Cl.
CPC .......... *A61B 5/4815* (2013.01); *A61B 5/0205* (2013.01); *A61B 5/4818* (2013.01);
(Continued)

(58) Field of Classification Search
None
See application file for complete search history.

(56) References Cited

U.S. PATENT DOCUMENTS 4,765,340 A    8/1988  Sakai
5,540,733 A *  7/1996  Testerman ........... A61B 5/1135
                                                         607/42

(Continued)

FOREIGN PATENT DOCUMENTS

CN    101340869    1/2009
CN    103767710    5/2014
(Continued)

OTHER PUBLICATIONS

Machine Translated Chinese Search Report Corresponding to Application No. 201880068114.6 dated May 16, 2022.
(Continued)

*Primary Examiner* — Carl H Layno
*Assistant Examiner* — Manolis Pahakis
(74) *Attorney, Agent, or Firm* — Dority & Manning, P.A.

(57) ABSTRACT

Approaches to determining a sleep fitness score for a user are provided, such as may be based upon monitored breathing disturbances of a user. The system receives user state data generated over a time period by a combination of sensors provided via a wearable tracker associated with the user. A system can use this information to calculate a sleep fitness score, breathing disturbance score, or other such value. The system can classify every minute within the time period as either normal or atypical, for example, and may provide such information for presentation to the user.

20 Claims, 9 Drawing Sheets

Related U.S. Application Data continuation of application No. 15/998,491, filed on Aug. 16, 2018, now abandoned.

(60) Provisional application No. 62/547,710, filed on Aug. 18, 2017.

(51) Int. Cl.

| | | |
|---|---|---|
| *A61B 5/08* | (2006.01) | |
| *A61B 5/024* | (2006.01) | |
| *A61B 5/06* | (2006.01) | |
| *A61B 5/01* | (2006.01) | |
| *A61B 5/145* | (2006.01) | |
| *A61B 5/369* | (2021.01) | |
| *A61B 5/389* | (2021.01) | |

(52) U.S. Cl.
CPC .......... *A61B 5/7264* (2013.01); *A61B 5/7267* (2013.01); *A61B 5/01* (2013.01); *A61B 5/02405* (2013.01); *A61B 5/02427* (2013.01); *A61B 5/067* (2013.01); *A61B 5/082* (2013.01); *A61B 5/0816* (2013.01); *A61B 5/14532* (2013.01); *A61B 5/14539* (2013.01); *A61B 5/14542* (2013.01); *A61B 5/369* (2021.01); *A61B 5/389* (2021.01); *A61B 5/4809* (2013.01); *A61B 5/4812* (2013.01); *A61B 5/681* (2013.01); *A61B 2562/0219* (2013.01)

(56) References Cited

U.S. PATENT DOCUMENTS

| | | | |
|---|---|---|---|
| 6,306,088 B1* | 10/2001 | Krausman | A61B 5/02055 600/534 |
| 7,294,112 B1* | 11/2007 | Dunlop | A61B 5/4809 600/595 |
| 8,636,667 B2 | 1/2014 | Ochs | A61B 5/02416 600/323 |
| 10,111,615 B2* | 10/2018 | Russell | A61B 5/6824 |
| 10,311,745 B2 | 6/2019 | Arnold | |
| 10,835,131 B2* | 11/2020 | Osorio | A61B 5/374 |
| 10,885,152 B2* | 1/2021 | Heneghan | A61B 5/4815 |
| 2004/0087878 A1 | 6/2004 | Krausman et al. | |
| 2004/0215095 A1 | 10/2004 | Lee et al. | |
| 2005/0113650 A1 | 5/2005 | Pacione | |
| 2005/0113709 A1* | 5/2005 | Millet | A61B 5/4818 600/529 |
| 2006/0173257 A1* | 8/2006 | Nagai | A61B 5/14551 600/323 |
| 2008/0287751 A1 | 11/2008 | Stivoric | |
| 2009/0203972 A1 | 8/2009 | Heneghan | |
| 2010/0204586 A1 | 8/2010 | Pu et al. | |
| 2011/0112442 A1 | 5/2011 | Meger | |
| 2012/0190948 A1* | 7/2012 | Vetter | A61B 5/7221 600/324 |
| 2013/0276785 A1* | 10/2013 | Melker | A61B 5/0205 128/204.23 |
| 2014/0135612 A1 | 5/2014 | Yuen | |
| 2014/0275850 A1 | 9/2014 | Venkatraman | |
| 2014/0343371 A1 | 11/2014 | Sowers | |
| 2015/0065832 A1 | 3/2015 | Manion | |
| 2015/0164375 A1 | 6/2015 | Schindhelm | |
| 2016/0015314 A1 | 1/2016 | Dusanter | |
| 2016/0022201 A1 | 1/2016 | Arnold | |
| 2016/0022203 A1 | 1/2016 | Arnold et al. | |
| 2016/0022205 A1* | 1/2016 | Remmers | A61B 5/7264 600/301 |
| 2016/0051184 A1 | 2/2016 | Wisbey | |
| 2016/0113526 A1 | 4/2016 | Nageshwar et al. | |
| 2016/0151603 A1* | 6/2016 | Shouldice | A61B 5/4806 600/26 |
| 2016/0270718 A1* | 9/2016 | Heneghan | A61M 16/0069 |
| 2016/0287122 A1 | 10/2016 | Heneghan | |
| 2017/0014035 A1 | 1/2017 | Newberry | |
| 2018/0064388 A1 | 3/2018 | Heneghan | |
| 2019/0000350 A1 | 1/2019 | Narayan | |
| 2019/0083034 A1* | 3/2019 | Shim | A61B 5/14551 |
| 2022/0392590 A1* | 12/2022 | Winstrom | G16H 80/00 |

FOREIGN PATENT DOCUMENTS

| | | |
|---|---|---|
| CN | 106580325 | 4/2017 |
| EP | 2687154 | 1/2014 |
| WO | WO2008029399 | 3/2008 |
| WO | 2011-087927 | 7/2011 |

OTHER PUBLICATIONS

Behar et al., "SleepAp: An Automated Obstructive Sleep Apnoea Screening Application for Smartphones", IEEE Journal of Biomedical and Health Informatics, vol. 19, No. 1, Jan. 1, 2015, pp. 325-331.
Zhang et al., "RASS: A Portable Real-Time Automatic Sleep Scoring System", 2012 IEEE 33$^{rd}$ Real-Time Systems Symposium, Dec. 4, 2012, pp. 105-114.
Non-Final Office Action issued in U.S. Appl. No. 15/998,491 dated Aug. 2, 2019.
International Search Report and Written Opinion issued in Application No. PCT/US2018/046963 dated Dec. 20, 2018.
Non-Final Office Action issued in U.S. Appl. No. 16/428,412 dated Aug. 2, 2019.
Final Office Action issued in U.S. Appl. No. 16/428,412 dated Feb. 7, 2020.
Notice of Allowance issued in U.S. Appl. No. 16/428,412 dated Sep. 1, 2020.

\* cited by examiner

AUTOMATED DETECTION OF BREATHING DISTURBANCES

CROSS-REFERENCE TO RELATED APPLICATIONS

This application is a continuation of U.S. application Ser. No. 16/428,412, filed May 31, 2019, now U.S. Pat. No. 10,874,345, and entitled "Automatic Detection of Breathing Disturbances," which claims priority to U.S. application Ser. No. 15/998,491 filed Aug. 16, 2018, and entitled "Automatic Detection of Breathing, Disturbances," which claims priority to U.S. Provisional Patent Application Ser. No. 62/547,710, filed Aug. 18, 2017, entitled "Automatic Detection of Breathing Disturbances," which are hereby incorporated herein by reference in their entirety for all purposes.

TECHNICAL FIELD

This disclosure relates to the field of wearable devices, and particularly to techniques for detecting breathing-related issues using one or more sensors of such devices.

BACKGROUND OF THE DISCLOSURE

Wearable electronic devices have gained popularity among consumers. A wearable electronic device may track a user's activities using a variety of sensors. Data captured from these sensors can be analyzed in order to provide a user with information that can help the user to maintain a healthy life style. In order to determine information about a user's activities, a conventional wearable electronic device collects activity data and runs computations on that data. Difficulty is encountered in obtaining accurate determinations of a user's activities, however, as these wearable electronic devices, being made to be worn by a user, are typically packaged in a compact casing with limited internal space. This limited space results in the devices containing less powerful components, such as processors, than would be possible in larger electronic devices. This limits the ability of these devices to run complex computations or perform complex operations. Further, conventional wearable electronic devices are subject to considerable incidental movements and noise, which can impact the inclusion or use of various components in these devices.

Wearable electronic devices can track metrics related to particular activities, such as a step count metric for running and walking activities. Other metrics that may be tracked by a wearable electronic device include metrics related to sleep. Typically, to initiate tracking of sleep metrics, a wearable electronic device provides an interface enabling the user to provide a manual indication that the user plans to go to sleep. For example, the wearable electronic device may include a physical or digital button that the user can push or tap to indicate that he or she is about to go to sleep. The timing of this action may be significantly different than when the user actually sleeps, and does not account for periods when the user is awake unless the user manually indicates that the user is now awake.

BRIEF SUMMARY OF THE DISCLOSURE

Approaches in accordance with various embodiments provide for the monitoring of breathing data for a user. Such information may be obtained by a monitoring system or device, and can be used to determine various patterns, trends, or aspects of the user's breathing, which can be indicative of breathing disturbances or other irregularities of a user, such as during a period of sleep.

Such a system may include a wearable activity tracker, or other wearable electronic device, configured to be worn on a wrist or other part of a user's body. The device can be in communication with a separate computing device, such as a smart phone or other mobile computing device, configured to execute a mobile application to process or collect at least a portion of the user data. The computing device and/or tracker can also be in communication with at least one server or remote computing system in various embodiments, such as to offload at least some of the processing or persistently store the user or result data.

A wearable activity tracker in at least one embodiment may include: at least one green photoplethysmographic (PPG) sensor configured to generate first PPG data; at least one red PPG sensor configured to generate second PPG data; at least one infrared PPG sensor configured to generate third PPG data; at least one accelerometer configured to generate acceleration data useful for determining motion; and at least one processor configured to generate a set of features based on the first PPG data, the second PPG data, the third PPG data, and the accelerometer data. The mobile application, when executed by the mobile device, may configure the mobile device to receive the set of features from the wearable activity tracker and wirelessly transmit the set of features to a server. The server may be in communication with the mobile device and further configured to: receive the set of features from the mobile device; determine, based on a first subset of the set of features relating to the accelerometer data, a sleep period during which the user of the wearable activity tracker was asleep; for each respective minute of a plurality of minutes within the sleep period, classify the respective minute as one of (i) a normal minute or (ii) a breathing disturbed minute, based on a second subset of the set of features corresponding to the first, second, and third PPG data generated during the respective minute and data corresponding to a time period outside the sleep period; generate a breathing disturbance score (or other breathing-related score such as a sleep fitness score) for the sleep period based on the classification of the plurality of minutes within the sleep period; and update a benchmark breathing disturbance score associated with a user category corresponding to the user based on the generated breathing disturbance score. The mobile application may further configure the mobile device to receive the determined score(s) from the server and cause the score(s) to be displayed on a display screen of the mobile device, or otherwise made available to a respective user, along with the updated benchmark breathing, sleep fitness, or other such score associated with the user category.

Such a system can have any sub-combination of the above-mentioned and other device sensors. In some embodiments, at least a subset of the green, red, and/or infrared PPG sensors, as well as the accelerometer(s), are located on the same side of the user's wrist when the wearable activity tracker is worn on the wrist of the user. The system can include a sensor, such as a bed sensor, that is configured to generate respiration data indicative of the user's respiration rate (additionally or alternatively, heart rate and heart beat-to-beat interval), wherein the server can further be configured to classify each respective minute based on the respiration data. The server can be configured to maintain past breathing disturbance scores for a plurality of users each associated with respective wearable activity trackers, which can be used for comparison purposes in at least some embodiments and where such usage of the data is permitted.

At least one processor of the wearable activity tracker can also be configured to determine when the accelerometer data indicates at least a threshold level of movement for a threshold amount of time, and to deactivate at least some of the at least one green PPG sensor, the at least one red PPG sensor, the at least one infrared PPG sensor.

Approaches in accordance with various embodiments can facilitate monitoring of breathing disturbances of a user of a wearable device. One example approach can include receiving sensor data generated by one or more sensors of the wearable device worn by the user, the one or more sensors comprising at least one accelerometer, the sensor data comprising accelerometer data indicative of movement of the user. Based at least in part on the accelerometer data, a sleep period can be determined that corresponds to a portion of the accelerometer data indicative of movement that is consistent with the user sleeping. For each respective temporal window of a plurality of temporal windows within the sleep period, the respective temporal window can be classified, such as for one of (i) breathing disturbed or (ii) breathing not disturbed (or regular), based on the sensor data generated during the respective temporal window and data corresponding to a time period outside the sleep period. A breathing disturbance score, sleep fitness score, or other such value can be determined based on the classification of the plurality of temporal windows, with the score(s) being output for presentation to the user.

Approaches in accordance with various embodiments can have any sub-combination of the following features: where the method further includes causing the breathing disturbance score of the user to be rendered on a display screen of a mobile device wirelessly paired with the wearable device along with a benchmark disturbance score corresponding to the user; where the method further includes determining a percentage of temporal windows classified as breathing disturbed out of the plurality of temporal windows, and selecting the breathing disturbance score from a plurality of breathing disturbance scores based on the percentage; where the method further includes receiving additional sensor data generated by at least one of the one or more sensors of the wearable device, wherein the additional sensor data is generated during a second period outside the sleep period, determining a baseline physiological metric associated with the user based on the additional sensor data, and classifying said each respective temporal window further based on the baseline physiological metric associated with the user; where the method further includes determining, based on the sensor data, that the sleep period is associated with movement less than a threshold level and that a second period outside the sleep period is associated with movement greater than the threshold level, and classifying one or more temporal windows within the sleep without classifying any temporal window within the second period outside the sleep period; where the method further includes causing an indication of how each temporal window within the sleep period is classified to be displayed in a user interface such that the user interface does not include an indication of how one or more temporal windows within the second period are classified; where the method further includes outputting the breathing disturbance score based on a determination that the sleep period is longer than a threshold amount of time; where the method further includes determining respiration rate data for the sleep period based on the sensor data, and classifying a first temporal window of the plurality of temporal windows as breathing disturbed based on a determination that a portion of the respiration rate data corresponding to the first temporal window includes a pattern of low values followed by a spike in value; where the sensor data includes first sensor data generated by at least one red PPG sensor and second sensor data generated by at least one green PPG sensor, the method further including increasing a first weight assigned to the first sensor data based on a determination that the second sensor data has not changed more than a threshold amount for a threshold amount of time; where the sensor data includes first sensor data generated by one or more PPG sensors and second sensor data generated by one or more motion sensors, the method further including classifying said each respective temporal window based on both of the first sensor data and the second sensor data; and where the sensor data includes first sensor data generated by a red PPG sensor and second sensor data generated by an infrared PPG sensor, the method further including extracting a low-frequency component of the first sensor data and a low-frequency component of the second sensor data, determining processed sensor data based on dividing the low-frequency component of the first sensor data by the low-frequency component of the second sensor data, and classifying at least one of the plurality of temporal windows based on the processed sensor data.

One aspect of the disclosure provides non-transitory physical computer storage storing instructions. The instructions may, when executed by one or more processors, configure the one or more processors to: receive sensor data generated by one or more sensors of a wearable device worn by a user, the one or more sensors comprising at least one accelerometer, the sensor data comprising accelerometer data indicative of movement of the user; determine, based on the accelerometer data, a sleep period corresponding to a portion of the accelerometer data indicative of movement that is consistent with the user sleeping; for each respective temporal window of a plurality of temporal windows within the sleep period, classify the respective temporal window as one of (i) breathing disturbed or (ii) not breathing disturbed, based on the sensor data generated during the respective temporal window and data corresponding to a time period outside the sleep period; determine a breathing disturbance score based on the classification of the plurality of temporal windows; and output the breathing disturbance score for presentation to the user.

Such a non-transitory physical computer storage in accordance with various embodiments can have any sub-combination of the following features: where the instructions, when executed by the at least one processor, further configure the at least one processor to classify said each respective temporal window further based on a determination that a portion of the accelerometer data corresponding to the respective temporal window is indicative of movement less than a threshold level; where the instructions, when executed by the at least one processor, further configure the at least one processor to wirelessly transmit the breathing disturbance score to a cloud service for storage in association with the user; and where the instructions, when executed by the at least one processor, further configure the at least one processor to receive a plurality of past breathing disturbance scores associated with the user from the cloud service, and to render a history of breathing disturbance scores on a display screen of a mobile device wirelessly paired with the wearable device based on the plurality of past breathing disturbance scores received from the cloud service.

BRIEF DESCRIPTION OF THE DRAWINGS

The embodiments described herein are illustrated by way of example, and not by way of limitation, in the figures of the accompanying drawings in which like references indicate similar elements.

DETAILED DESCRIPTION

Approaches in accordance with various embodiments can obtain and analyze health-related information for a user wearing, or otherwise utilizing, a device such as a wearable tracking device. A tracking device in some embodiments can include one or more sensors for tracking of an activity performed by a user of a wearable device. Some example wearable devices may be referred to as wearable activity trackers or wearable activity tracking devices. Various algorithms or techniques for tracking activities have been developed, and these algorithms may be specialized based on the type of activity performed by the user. For example, the user may wear the wearable device all day, and for each activity performed by the user throughout the day and night, a specialized algorithm may generate and present relevant activity metrics to the user. For example, the wearable device may collect sensor data from one or more sensors provided on the wearable device while the user is sleeping, and generate and present information such as a sleep score indicative of how well the user is sleeping each night.

Figure 1A:
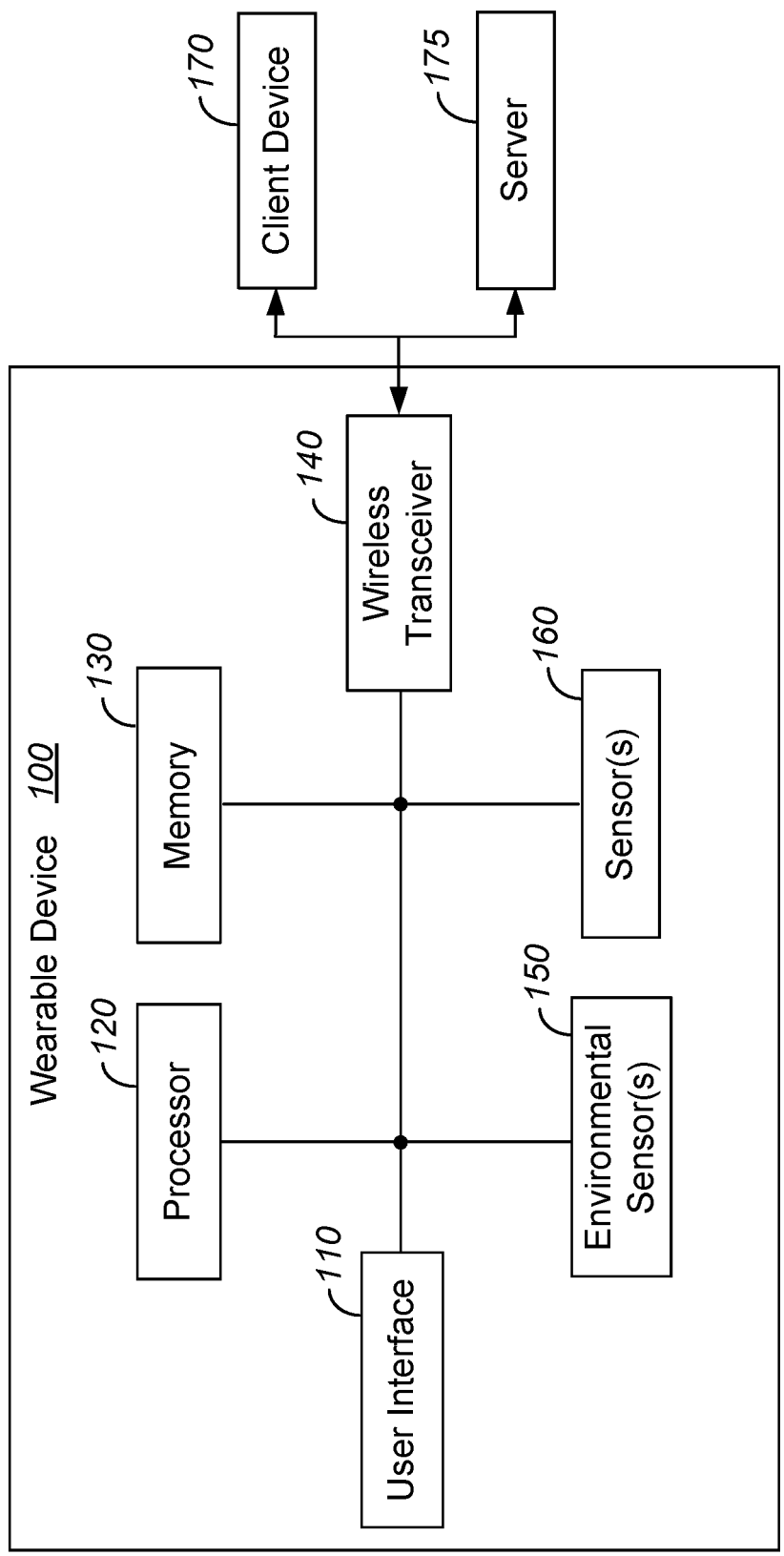
FIG. 1A is a block diagram illustrating certain components of an example wearable device in accordance with aspects of this disclosure.

FIG. 1A is a block diagram illustrating an example wearable device in accordance with aspects of this disclosure. The wearable device 100 may include a processor 120 (which may be a set of processors), a memory 130, a wireless transceiver 140, and one or more sensor(s) 160. The wearable device 100 may also optionally include a user interface 110 and one or more environmental sensor(s) 150. The wireless transceiver 140 may be configured to wirelessly communicate with a client device 170 and/or server 175, for example, either directly or when in range of a wireless access point (not illustrated) (e.g., via a personal area network (PAN) such as Bluetooth pairing, via a wireless local area network (WLAN), via wide area network (WAN), etc.). Each of the memory 130, the wireless transceiver 140, the one or more sensor(s) 160, the user interface 110, and/or the one or more environmental sensor(s) 150 may be in electrical communication with the processor 120. The client device 170 may be a smartphone, a tablet, or another mobile device executing software (e.g., a mobile application) configured to perform one or more techniques described herein. The server 175 may be implemented using one or more computing devices executing software configured to perform one or more techniques described herein. The techniques described herein may be performed by the wearable device 100, the client device 170, and the server 175 in a distributed manner. The wearable device 100 (also referred to herein as wearable activity tracker) may be any of a smartwatch, a watch, a wrist-wearable fitness-, health-, or activity-monitoring device, and the like, although the concepts described herein may be implemented on any type of portable or wearable devices including one or more sensors.

The memory 130 may store instructions for causing the processor 120 to perform certain actions. In some embodiments, the sensors 160 may include one or more of biometric sensors, optical sensors (e.g., a photoplethysmographic (PPG) sensor), motion sensors or inertial sensors (e.g., accelerometer, gyroscope, digital compass, etc.), barometric sensors (e.g., altimeter, etc.), geolocation sensors (e.g., GPS receiver), and/or other sensor(s). Further information regarding such sensors are described in more detail below (e.g., in connection with FIG. 1B).

The wearable device 100 may collect one or more types of physiological and/or environmental data from the one or more sensor(s) 160, the one or more environmental sensor(s) 150, and/or external devices and communicate or relay such information to other devices (e.g., the client device 170 and/or the server 175), thus permitting the collected data to be viewed, for example, using a web browser or network-based application, such as for an individual account or shared account, or shared via social media where permitted or approved by the user. As used herein, the term "collect," in addition to having its ordinary meaning, may be used interchangeably with "determine," "extract," "calculate," "generate", etc. to refer to the steps performed to arrive at the desired data (e.g., breathing disturbance metrics). For example, while being worn by the user, the wearable device 100 may perform biometric monitoring via calculating and storing the user's step count using the one or more sensor(s) 160. The wearable device 100 may transmit data representative of the user's step count to an account on a web service (e.g., fitbit.com), computer, mobile phone, and/or health station where the data may be stored, processed, and/or visualized by the user. The wearable device 100 may measure or calculate other physiological metric(s) in addition to, or in place of, the user's step count. Such physiological metric(s) may include, but are not limited to: energy expenditure, e.g., calorie burn; floors climbed and/or descended; heart rate; heartbeat waveform; heart rate variability; heart rate recovery; respiration, oxygen saturation (SpO$_2$), blood volume, blood glucose, skin moisture and skin pigmentation level, location and/or heading (e.g., via a GPS, global navigation satellite system (GLONASS), or a similar system); elevation; ambulatory speed and/or distance traveled; blood pressure; blood glucose; skin conduction; skin and/or body temperature; muscle state measured via electromyography; brain activity as measured by electroencephalography; weight; body fat; caloric intake; nutritional intake from food; medication intake; sleep periods (e.g., clock time, sleep phases, sleep quality and/or duration); pH levels; hydration levels; respiration rate; and/or other physiological metrics.

The wearable device 100 may also measure or calculate metrics related to the environment around the user (e.g., with the one or more environmental sensor(s) 150), such as, for example, barometric pressure, weather conditions (e.g., temperature, humidity, pollen count, air quality, rain/snow conditions, wind speed), light exposure (e.g., ambient light, ultra-violet (UV) light exposure, time and/or duration spent in darkness), noise exposure, radiation exposure, and/or magnetic field. Furthermore, the wearable device 100 (and/or the client device 170 and/or the server 175) may collect data from the sensor(s) 160 and/or the environmental sensor(s) 150, and may calculate metrics derived from such data. For example, the wearable device 100 (and/or the client device 170 and/or the server 175) may calculate the user's stress or relaxation levels based on a combination of heart rate variability, skin conduction, noise pollution, and/or sleep quality. In another example, the wearable device 100 (and/or the client device 170 and/or the server 175) may determine the efficacy of a medical intervention, for example, medication, based on a combination of data relating to medication intake, sleep, and/or activity. In yet another example, the wearable device 100 (and/or the client device 170 and/or the server 22) may determine the efficacy of an allergy medication based on a combination of data relating to pollen levels, medication intake, sleep and/or activity. These examples are provided for illustration only and are not intended to be limiting or exhaustive.

Figure 1B:
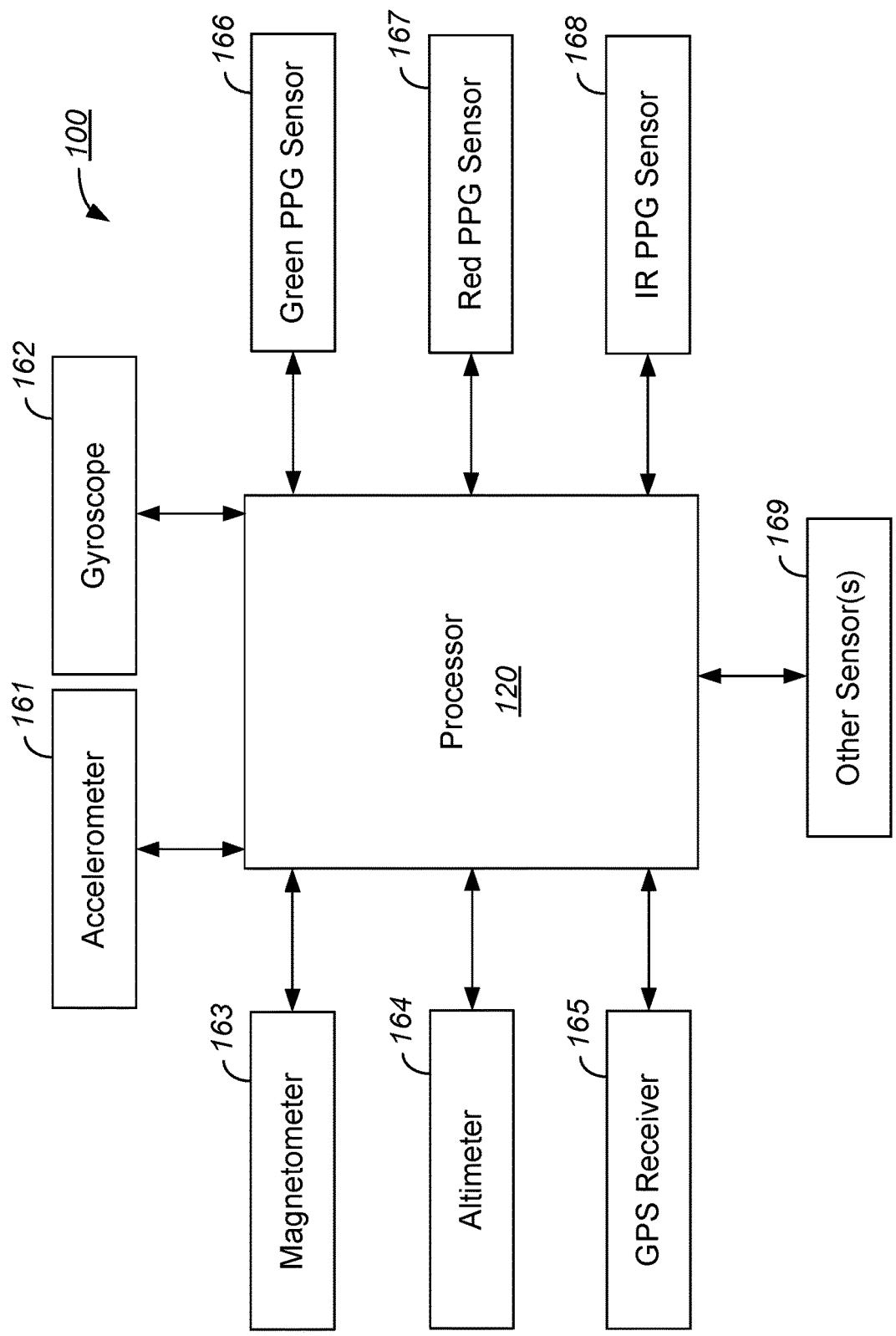
FIG. 1B is a block diagram illustrating example sensors which may be in communication with a processor of a wearable device in accordance with aspects of this disclosure.

FIG. 1B is a block diagram illustrating a number of example sensors that may be included in the wearable device 100 in accordance with aspects of this disclosure. For example, in the embodiment of FIG. 1B, the wearable device 100 includes an accelerometer 161 (e.g., a multi-axis accelerometer), a gyroscope 162, a magnetometer 163, an altimeter 164, a GPS receiver 165, a green PPG sensor 166, a red PPG sensor 167, an infrared (IR) PPG sensor 168, and one or more other sensors 167 (including but not limited to, e.g., a temperature sensor, an ambient light sensor, a galvanic skin response (GSR) sensor, a capacitive sensor, a humidity sensor, a sound sensor, a force sensor, a multi-axis accelerometer, a gravity sensor, a piezoelectric film sensor, a rotation vector sensor, etc.), all of which may be in communication with the processor 120. Each of the sensors illustrated in FIG. 1B may be in electrical communication with the processor 120. The processor 120 may use input received from any combination of the sensors in detecting the start of an exercise and/or in tracking the metrics for the exercise. One or more of the sensors described herein may not be within the wearable device 100. For example, these sensors may be placed on the chest of the user, the mattress or bedside table of the user, while the wearable device 100 is worn by the user.

Although the example of FIG. 1B illustrates sensors 161-169, in other embodiments the wearable device 100 may include a fewer number of sensors and/or any other subsets and combinations of the sensors (e.g., only the accelerometer 161, a combination of the accelerometer 161, red PPG sensor 167, and IR PPG 168, a combination of the accelerometer 161 and the green PPG sensor 166, etc.). The wearable device 100 may also include one or more additional sensors not illustrated in FIG. 1B.

Additionally, in some implementations the GPS receiver 165 may be located in the client device 170 rather than the wearable device 100. In these implementations, the processor 120 may wirelessly communicate with the client device 170 to control and/or receive geolocation data from the GPS receiver 165 and/or other geolocation sensor(s).

In related aspects, the processor 120 and other component(s) of the wearable device 100 (e.g., shown in FIGS. 1A and 1B) may be implemented using any of a variety of suitable circuitry, such as one or more microprocessors, application specific integrated circuits (ASICs), field programmable gate arrays (FPGAs), discrete logic, software, hardware, firmware or any combinations thereof. When the techniques are implemented partially in software, a device may store instructions for the software in a suitable, non-transitory computer-readable medium and execute the instructions in hardware using one or more processors to perform the techniques of this disclosure. In further related aspects, the processor 120 and other component(s) of the wearable device 100 may be implemented as a System-on-Chip (SoC) that may include one or more central processing unit (CPU) cores that use one or more reduced instruction set computing (RISC) instruction sets, a GPS receiver 165, a wireless wide area network (WWAN) radio circuit, a WLAN radio circuit, and/or other software and hardware to support the wearable device 100.

Figure 1C:
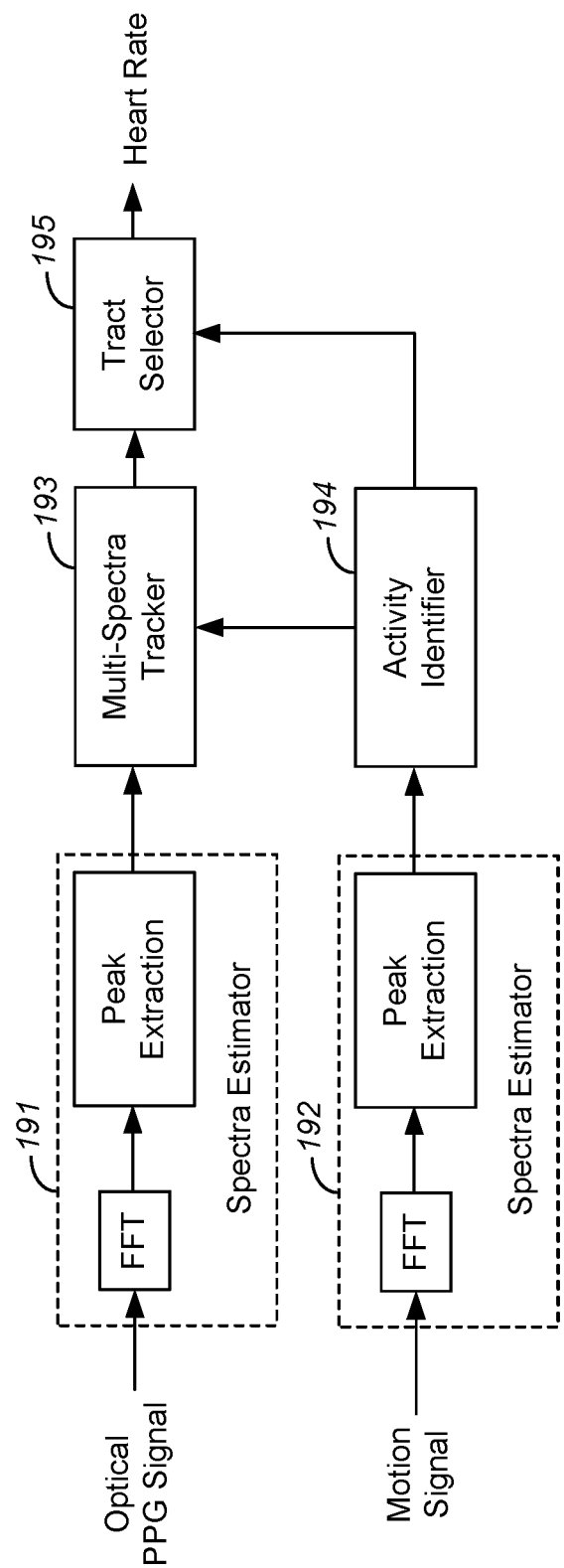
FIG. 1C is an example block diagram of a system used for determining a heart rate in accordance with aspects of this disclosure.

FIG. 1C is an example block diagram of a system used for determining heart rate in accordance with aspects of this disclosure. As shown in FIG. 1C, the wearable device 100 may include a system 190 of circuit components for determining the heart rate of the user based on an optical PPG signal (e.g., received from the green PPG sensor 166 of FIG. 1B) and a motion signal or signature (e.g., received from the accelerometer 161 of FIG. 1B). As used herein, a motion signature may refer to any biometric signature or signal that may be received from and/or based on output data from one or more of sensors, such as, for example, inertial sensor(s) (e.g., accelerometer(s) and gyroscope(s)), barometric sensors(s) (e.g., altimeter(s)), which may be indicative of the activity and/or physiological state of a user of the wearable device 100. The system 190 may be implemented by hardware components and/or in software executed by the processor 120. The system 190 may include first and second spectra estimators 191 and 192, a multi-spectra tracker 193, an activity identifier or discriminator 194, and a track selector 195. Each of the first and second spectra estimators 191 and 192 may include a Fast Fourier Transform (FFT) block and a peak extraction block. In the example of FIG. 1C, the activity identifier 194 may use the peaks extracted from the motion signature to determine the activity that the user is performing (e.g., sedentary, walking, running, sleeping, lying down, sitting, biking, typing, elliptical, weight training, swimming, etc.). This determination of the current activity of the user may be used by the multi-spectra tracker 193 and the track selector 195 in extracting the heart rate from the optical PPG signal. Thus, the motion signature in FIG. 1C may be used by the system 190 to determine the current activity of the user. In other embodiments, the processor 120 may use a similar technique to the activity identifier 194 in determining the type of an exercise, as discussed in greater detail below.

The blocks illustrated in FIG. 1C are merely examples of components and/or processing modules that may be performed to supplement a PPG signal with a motion signature to determine heart rate. However, in other implementations, the system 190 may include other blocks or may include input from other biometric sensors of the wearable device 100.

Under certain operating conditions, the heart rate of the user may be measured by counting the number of signal peaks within a time window or by utilizing the fundamental frequency or second harmonic of the signal (e.g., via an FFT). In other cases, such as heart rate data acquired while the user is in motion, FFTs may be performed on the signal and spectral peaks extracted, which may then be subsequently processed by a multiple-target tracker which starts, continues, merges, and/or deletes tracks of the spectra.

In some embodiments, a similar set of operations may be performed on the motion signature and the output may be used to perform activity discrimination which may be used to assist the multi-spectra tracker 193. For instance, it may be determined that the user was stationary and has begun to move. This information may be used by the multi-spectra tracker 193 to bias the track continuation toward increasing frequencies. Similarly, the activity identifier 194 may determine that the user has stopped running or is running slower and this information may be used to preferentially bias the track continuation toward decreasing frequencies.

Tracking may be performed by the multi-spectra tracker 193 with single-scan or multi-scan, multiple-target tracker topologies such as joint probabilistic data association trackers, multiple-hypothesis tracking, nearest neighbor, etc. Estimation and prediction in the tracker may be done through Kalman filters, spline regression, particle filters, interacting multiple model filters, etc.

The track selector 195 may use the output tracks from the multiple-spectra tracker 193 and estimate the user's heart rate based on the output tracks. The track selector 195 may estimate a probability for each of the tracks that the corresponding track is representative of the user's heart rate. The estimate may be taken as the track having the maximum probability of being representative of the user's heart rate, a sum of the tracks respectively weighted by their probabilities of being representative of the user's the heart rate, etc. The activity identifier 194 may determine a current activity being performed by the user which may be used by the track selector 195 in estimating the user's heart rate. For instance, when the user is sleeping, sitting, lying down, or sedentary, the user's estimated heart rate may be skewed toward heart rates in the 40-80 bpm range. When the user is running, jogging, or doing other vigorous exercise, the user's estimated heart rate may be skewed toward elevated heart rates in the 90-180 bpm range. The activity identifier 194 may determine the user's current activity (e.g., a current exercise) based at least in part on the speed of the user. The user's estimated heart rate may be shifted toward (or wholly obtained by) the fundamental frequency of the selected output track when the user is not moving. The output track that corresponds to the user's heart rate may be selected by the track selector 195 based on criteria that are indicative of changes in activity. For instance, when the user begins to walk from being stationary, the track selector 195 may select the output track that illustrates a shift toward higher frequency based on output received from the activity discriminator 194.

Although some embodiments of the present disclosure are described with respect to heart rate, the techniques described herein may be extended to other metrics. For example, sensor data generated by the one or more sensors described herein may be used to determine respiration, $SpO_2$, blood volume, blood glucose, skin moisture, and skin pigmentation level and, for example, utilize such metrics for activity detection/identification.

The motion sensor(s) of the wearable device 100 (e.g., a multi-axis accelerometer 161, a gyroscope 162, or another motion sensor) may generate motion data samples that represent motion for a plurality of time intervals (e.g., the motion sensor is inside the wearable device 100 and the motion data represent motion of the wearable device 100). The motion sensor may generate a number of motion data samples during a time interval. The number of samples generated in a time interval may depend on the sampling rate of the motion sensor and the length of time of the interval. In the case that the motion sensor is an accelerometer, the motion data samples may characterize a measurement of acceleration along an axis of movement. In some cases, a motion data sample may be a data value that consumes a given amount of storage (e.g., 64-bits, 32-bits, 16-bits, and so on). The amount of storage consumed by a sample may depend on the implementation of the motion sensor used in the embodiment and the communication interface used to transfer the samples from the motion sensor to memory accessible by the microprocessor of the wearable device.

The wearable device 100 may comprise one or more optical or electro-optical sensors, such as, for example, one or more PPG sensors. The PPG sensor(s) of the wearable device 100 (e.g., green PPG sensor 166, red PPG sensor 167, IR PPG sensor 168, etc.) may generate PPG data usable to calculate heart rate, heart rate variability, respiration rate, and/or oxygen saturation, among other things. PPG data can use used to calculate a user's heart rate by measuring the time between peaks or by calculating a dominant frequency in the optical signal. For most users, heart rate drops soon after onset of sleep and continues dropping over the course of sleep until early in the morning. Heart rate rises when the users wake up or during short disturbances during sleep. Measuring heart rate allows the system to better identify periods of sleep. Further, heart rate is a good indicator to separate periods of sleep from periods of lying still, which could confuse a motion sensor like an accelerometer. Some users do not see this characteristic drop in heart rate with sleep. Such users can be identified after they wear the wearable electronic device for a few days and a different algorithm can be used on such users.

The difference of a user's heart rate from his/her average resting heart rate can be used as a personalized measure of how low his/her heart rate has dropped. The PPG data can also be used to calculate the respiration rate of the user. Respiration rate often shows distinct changes with sleep and can be used as a feature to identify periods of sleep. Respiration can be calculated using a number of techniques: (i) measuring variabilities in the inter-peak intervals between heart beats, (ii) measuring slow variabilities (0.1-0.5 Hz) in the baseline of the PPG signal, and/or (iii) measuring slow periodic signals (0.1-0.5 Hz) in the acceleration signal.

In one embodiment, data representing the heart rate, heart rate variability, respiration rate, and/or oxygen saturation of the user of the wearable device 100 are calculated, and the resulting data is an additional input for classifying the temporal periods or generating the breathing disturbance score, according to embodiments of the present disclosure.

In various embodiments, the PPG sensors described herein may include one or more electronic semiconductor light sources, such as LEDs, or other light sources that produce light using any of filaments, phosphors, or laser. In some implementations, each light source of the wearable device 100 emits light having the same center wavelength or within the same wavelength range. In other cases, at least one light source may emit light having a center wavelength that is different from another light source. The center wavelengths of the light emitted by the one or more light sources may be in the range of 495 nm to 570 nm. For example, a particular green light source may emit light with a center wavelength of 525 nm (or approximately 525 nm). In other embodiments, one or more light sources may emit red light (e.g., 660 nm or approximately 660 nm center wavelength), and one or more light sources may emit IR light (e.g., 940 nm or approximately 940 nm center wavelength). In some embodiments, independent control of all light sources is provided. In other embodiments, several light sources are controlled together as a gang or bank.

The PPG sensors described herein may include one or more light detectors adapted to detect wavelengths of light emitted from light sources, including those reflected or passed through elements that may impact the wavelengths or other aspects of the light. One or more PPG sensors described herein may include a single light source and a single light detector. Alternatively, other PPG sensors described herein may include multiple light sources and/or multiple light detectors. A light detector, in an embodiment, may comprise one or more detectors for detecting each different wavelength of light that is used by the light sources. For example, a first detector may be configured to detect light with a wavelength of 660 nm (or approximately 660 nm), a second detector may be configured to detect light with a wavelength of 940 nm (or approximately 940 nm), and a third detector may be configured to detect light with a wavelength of 525 nm (or approximately 525 nm). Examples include photodiodes fabricated from semiconductor materials and having optical filters that admit only light of a particular wavelength or range of wavelengths. The light detectors may comprise any of a photodiode, phototransistor, charge-coupled device (CCD), thermopile detector, or complementary metal-oxide-semiconductor (CMOS) sensor. One or more of the light detectors may comprise a bandpass filter circuit.

Breathing and/or sleep disturbances may be prevalent in the general population. For example, sleep apnea may affect 3-7% of adults. Despite its prevalence, up to 80% of moderate and severe cases may be undiagnosed. Undiagnosed, sleep apnea is a risk factor in a variety of other conditions including coronary artery disease and type II diabetes. Diagnosing sleep apnea requires the equipment of a sleep laboratory, which can be expensive, time-consuming and disturb natural sleep due to numerous body-mounted sensors, which are part of the testing. Further, the severity of apnea can vary night to night and a full characterization of sleep apnea severity may require multi-night observations, which are unsuitable for sleep laboratories. A continuous, comfortable sleep monitoring system would allow the general population to screen for the risk of sleep apnea in their own homes without disturbing natural sleep. Such a system would also allow users to track the severity of apnea over time and determine which, if any, lifestyle choices contribute to breathing disturbances during sleep, e.g., obesity.

The disruption of normal breathing during sleep (or when the user is awake) can be detected in multiple ways using a variety of combinations of sensors. In some embodiments, sleep apnea or other sleep/breathing conditions can be detected based on the presence of any combination of the following indicators: (i) reduction in blood oxygenation using pulse oximetry (e.g., as part of a PPG system utilizing PPG data); (ii) disruption of normal audible breathing patterns as measured by an audio sensor; (iii) change in respiration rate as measured using the PPG system; (iv) change in respiration using a strain gauge (e.g., worn around the chest); (v) change in respiration using an accelerometer (that measures the periodic accelerations of respiration); (vi) change in respiration using a video camera that directly or indirectly observes respiration; and/or (vii) change in respiration using a $CO_2$ sensor that detects changes in expelled carbon dioxide.

Figure 2:
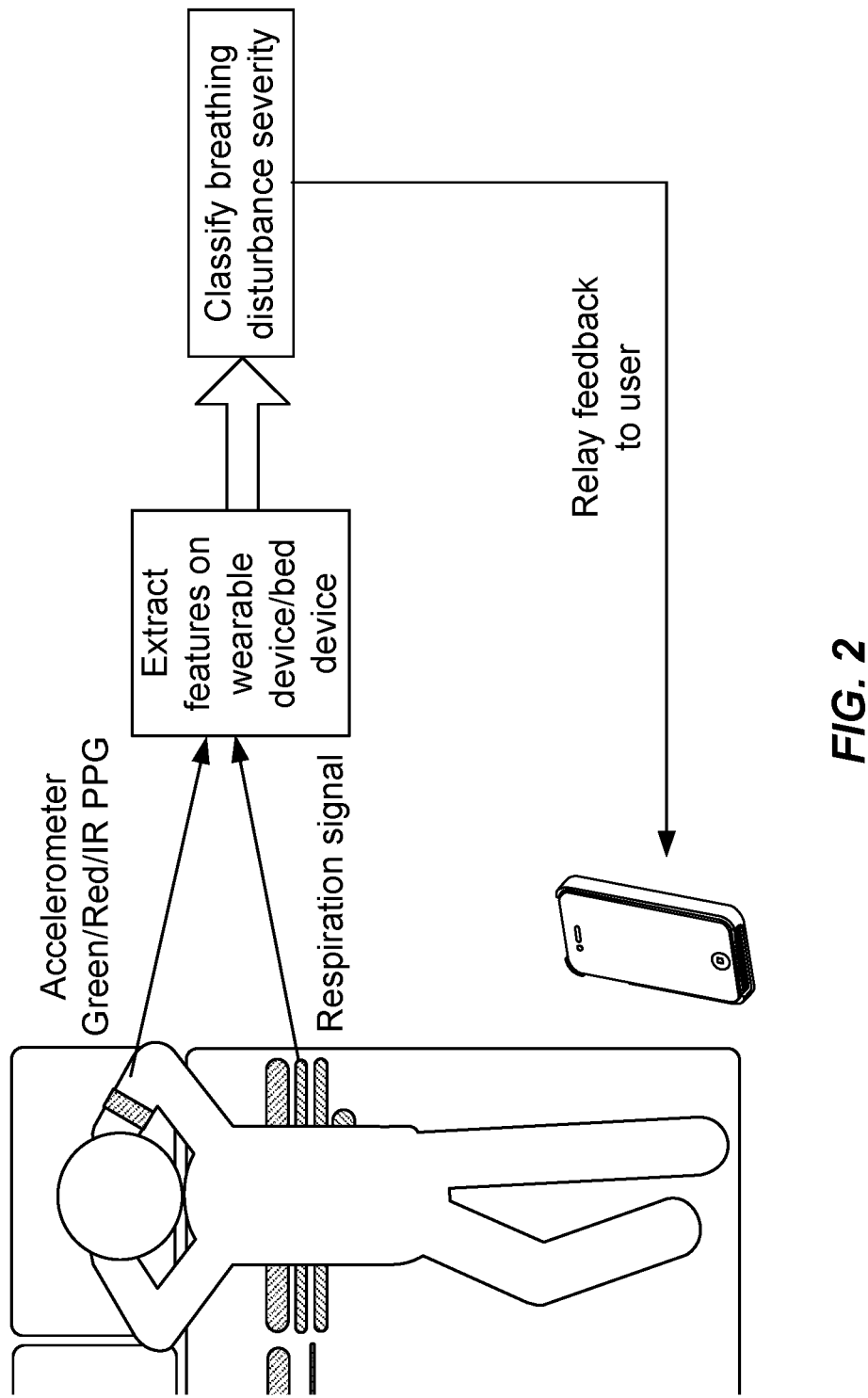
FIG. 2 illustrates an overview of a system for monitoring breathing disturbances in accordance with aspects of this disclosure.

A combination of non-invasive sensors coupled with machine learning algorithms can provide diagnostically relevant information. A device will be worn on a wrist wearable, which can sense blood flow using multiple optical wavelengths (red, infrared, and green) as well as acceleration due to motion. The green optical sensor enables monitoring of heart rate variability, and several measures of heart rate variability have been linked to the presence of breathing disturbances. The red and infrared optical sensors provide information about the level of blood oxygenation, which may decrease during apneas or hypopneas. A different package of sensors on the bed to sense position, movement, or respiratory effort may also be used in conjunction with the wrist wearable system. An overview of this system is illustrated by system 200 of FIG. 2.

In some embodiments, all of the sensors used for detecting breathing disturbances of a user are located on a wrist-worn device. For example, each sensor may be configured to generate sensor data from or near the wrist of the user. In one embodiment, the red PPG sensor 167 and the IR PPG sensor 168 are not located on the fingertip of the user. In another embodiment, the red PPG sensor 167 and the IR PPG sensor 168 are located on the fingertip of the user. In some embodiments, the sensor data generated by one or more of the sensors of the wearable device 100 is not sufficient to calculate the $SpO_2$ (e.g., to a medically acceptable degree of accuracy) due to the location from which the sensor data is gathered (e.g., the wrist of the user). In other embodiments, the sensor data generated by one or more of the sensors of the wearable device 100 (e.g., accelerometer 161) is sufficient to calculate the $SpO_2$. (e.g., to a medically acceptable degree of accuracy). The motion sensor of the wearable device 100 is configured to generate motion data from a location proximate to the location (e.g., adjacent, within the same housing, from the same side of the wrist, etc.) from which the PPG data is gathered (e.g., by one or more of the PPG sensors 166-168).

In one example, a mattress or bed sensor is sitting on top of the user's mattress. In another example, the mattress or bed sensor is inside the user's mattress. In yet another example, the mattress or bed sensor is underneath the user's mattress. In some cases, the detection of breathing disturbances is performed without sensor data from a mattress or bed sensor. In some cases, none of the wearable device 100, client device 170, and the server 175 is in communication with a mattress or bed sensor. Although a mattress or bed sensor is used as an example, any direct respiration sensor could be used instead or in addition (e.g., a chest strap inductance plethysmograph or an oronasal cannula). Additionally or alternatively, such a sensor may also generate heart rate and/or heart beat-to-beat interval, and the respiration data, heart rate data, and/or heart beat-to-beat interval data may be used in the classification of a given temporal window and/or generation of a breathing disturbance score.

In some embodiments, sensor data (e.g., accelerometer data, PPG data, etc.) or other physiological metrics generated during an active period during which the motion data (e.g., accelerometer data) indicates that the user is active is used for detecting breathing disturbances of the user during an inactive period during which the motion data indicates that the user is inactive (or in a sleep state). For example, if the motion data of a user generated during the user's active period indicates that the user is physically active (e.g., exercises frequently, has a high step count, etc.), the baseline heart rate or other threshold that may cause a temporal window to be classified as breathing disturbed may be increased (or decreased). Alternatively, if the motion data of a user generated during the user's active period indicates that the user is not physically active (e.g., does not exercise frequently, has a low step count, etc.), the baseline heart rate or other threshold that may cause a temporal window to be classified as breathing disturbed may be decreased (or increased).

In some embodiments, the classification of the temporal window and/or the detection of the user's sleep state is based on the wrist orientation data and/or the wrist movement data generated by the motion sensor of the wearable device 100 (e.g., accelerometer 161). For example, if the wrist orientation data indicates that the user's wrist is oriented in a way that is inconsistent with sleep during a specific period, then the user may be determined not to be in a sleep state during the specific period. In another example, if the wrist movement data indicates that the user is moving around, the baseline heart rate or other threshold that may cause a temporal window to be classified as breathing disturbed may be increased.

In some embodiments, the PPG data generated by one or more of the PPG sensors of the wearable device 100 is filtered such that any PPG data during a specific period in which motion data (e.g., accelerometer data) indicates a high level of user movement is removed (or not considered for detecting breathing disturbances of the user). In some embodiments, only the PPG data generated during a period having motion data below a threshold is kept and utilized for detection of breathing disturbances of the user.

Figure 3:
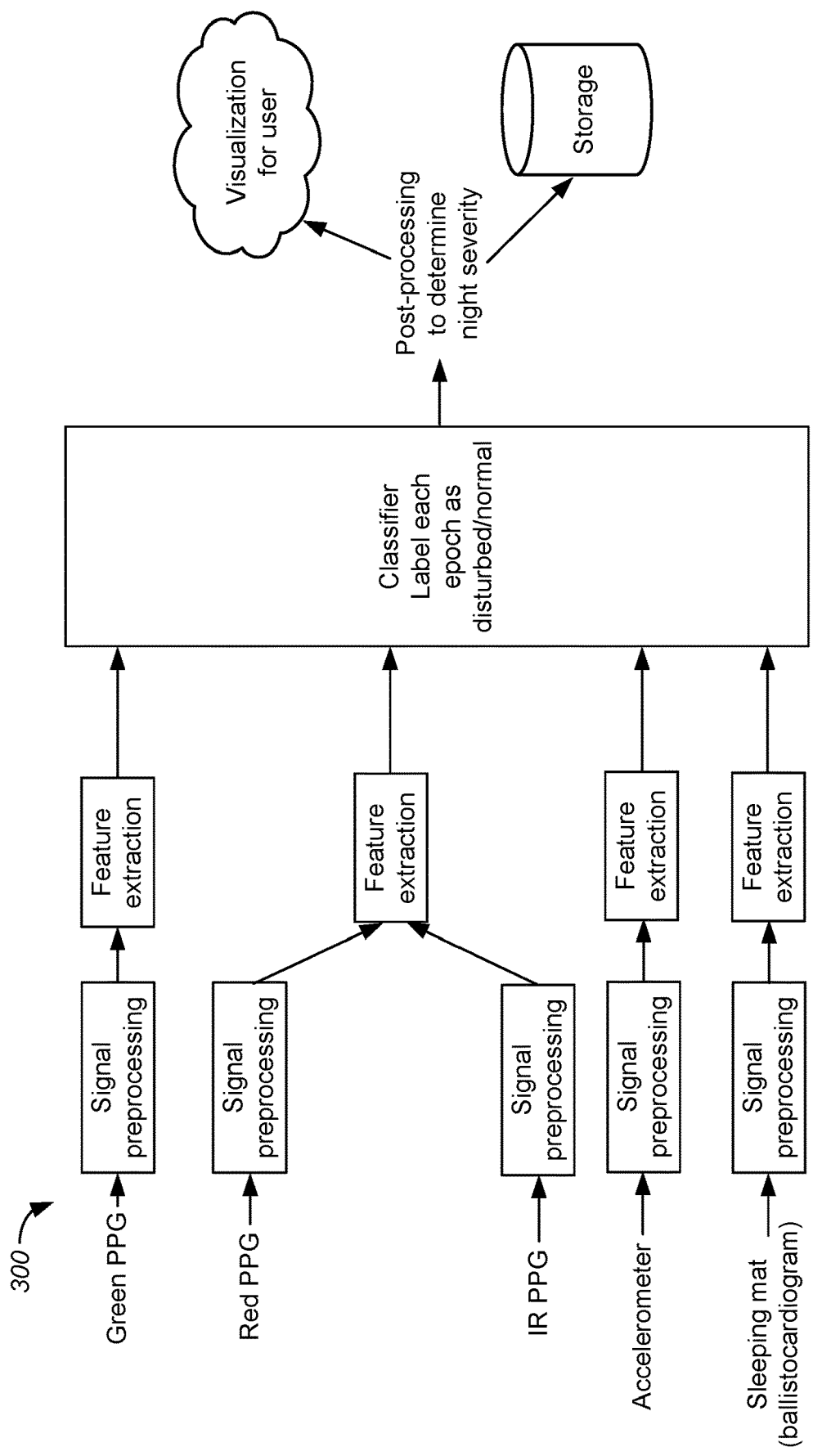
FIG. 3 illustrates an overview of the signal processing performed by the system of FIG. 2 in accordance with aspects of this disclosure.

Data from these different sensor streams are extracted using novel feature extraction algorithms. Features related to heart rate variability (e.g., calculated based on the sensor data from the green PPG sensor 166), SpO$_2$ or an indicator thereof (e.g., calculated based on the sensor data from the red PPG sensor 167 and the IR PPG sensor 168), movement (e.g., accelerometer data), and/or respiration (e.g., sensor data from the mattress or bed sensor) are extracted each minute and processed by a classification algorithm to determine if the minute is breathing disturbed or normal. Sensor data from the mattress or bed sensor and/or the accelerometer can be used to determine the onset and end of sleep. A high-level overview of the signal processing chain is illustrated by system 300 of FIG. 3.

Features extracted from the sensor data may comprise various indicators used for classifying each temporal window as either breathing disturbed or normal. In some embodiments, these features may be extracted from each overlapping window of time, where each overlapping window of time includes a number of samples (e.g., sensor readings). In some embodiments, the extracted features include one or more of the mean of the samples, the standard deviation of the samples, the energy of the samples, the maximum of the samples, the minimum of the samples, the difference between the maximum and the minimum, the root mean square of the samples, the count of oscillations of the samples, the AC signal (e.g., high-frequency component) of the samples, the DC (e.g., low-frequency component) signal of the samples, etc. In one embodiment, the extracted features are combined using a linear weighting function to form a discriminant value. For example, if the features for a temporal window are labeled as x1, x2, x3, etc., then the weighted sum is calculated as w1x1+w2x2+w3x3+ . . . =d, where d is called the discriminant value. This value is compared to a threshold which separates "breathing disturbed" epochs (or temporal windows) from "non-breathing-disturbed" epochs (or temporal windows). The threshold is determined using a set of training data where these labels have been previously calculated by a human expert, or other means.

In some embodiments, a set of data is collected from a sleep lab where a sleep expert has labeled the data, and the system creates, based on the collected set of data, a dictionary of what the extracted features look like in the normal case (e.g., during a non-breathing-disturbed temporal window) and the breathing disturbed case (e.g., during a breathing-disturbed temporal window). The system compares the features extracted from a given set of sensor data to the dictionary, and determines whether the extracted features are more similar to those corresponding to the normal case or those corresponding to the breathing disturbed case.

The extracted features may be further processed and compared against a set of threshold values for determining whether a given temporal window is breathing disturbed or not. For example, the DC signal of the sensor data from the red PPG sensor 167 divided by the DC signal of the sensor data from the IR PPG sensor 168 may be graphed, and any temporal window having a relatively static value (e.g., between specific low and high threshold values) for a threshold amount of time may be classified as breathing disturbed. In some embodiments, the system may split the signal generated by each of the red and IR sensors into a motion-sensitive component and a motion-insensitive component, and use only the motion-insensitive component (and not the motion-sensitive component) in classifying the temporal window as breathing disturbed or not. In some embodiments, the system may split the signal generated by each of the red and IR sensors into an arterial (or blood) oxygenation component and a tissue (or other) oxygenation component, and use only the tissue oxygenation component (and not the arterial oxygenation component) in classifying the temporal window as breathing disturbed or not. In some embodiments, the system classifies the temporal window as breathing disturbed based on detecting a pattern of low respiration (below a threshold level of respiration over a threshold amount of time). In some embodiments, the system classifies the temporal window as breathing disturbed based on detecting a spike in respiration (e.g., indicative of a big gasp).

Other data collected from the motion sensors, PPG sensors, and other sensors may include: (i) measures of user movement; (ii) data for calculating heart rate, heart rate variability, and respiration; and (iii) time-domain or frequency-domain measure of heart rate variability. The raw heart rate data can be used to define a number of higher-level features. For example: (i) rolling median or average heart rate on various timescales (e.g., over the last minute, last 5 minutes, etc.); (ii) rolling quantile of the heart rate distribution as measured on various timescales; and (iii) whether heart rate exceeded/went-below some threshold over the course of some interval.

Additionally, statistical features may be derived using time derivative of heart rate. For example: (i) rolling maximum change in heart rate over various timescales; and (ii) rolling median, average, or some other quartile of the distribution of heart rate derivative over various timescales. Similar statistical features can be derived using heart rate variability or respiration. For example: (i) number of times HRV or respiration events exceeded some threshold over various timescales; and (ii) rolling median, average, or some other quartile of the distribution of HRV or respiration over various timescales. Heart rate, the derivative of heart rate, heart rate variability, and respiration may be normalized or standardized appropriately on a per-user basis account for natural variation across users. For example, a user's resting heart rate may be subtracted from his or her instantaneous heart rate. Demographic information may also be used to renormalize features to account for variation according to demographics.

These statistical features may be used to train a classifier to classify temporal windows as either breathing disturbed or normal. In one embodiment, the system uses a random forest classifier. Other classification methods include neural networks, hidden-Markov models, support vector machines, k-mean clustering, and decision trees.

In some embodiments, the machine-learning-based classifier system may flexibly use or not use particular sensor inputs as they are available, without changing the underlying model. Thus, the same system could be used with a combination of wrist-worn sensors and external sensors, just with the wrist-worn sensors, just with one or more PPG sensors and a motion sensor, or just with one or more PPG sensors. In some embodiments, the system uses all of the sensor data available. For example, if four sensors are generating (or generated) sensor data, sensor data from all four sensors are used to classify the temporal window as breathing disturbed or not. In another example, if three of the four sensors are generating (or generated) sensor data and one of the four sensors is not generating (or did not generate) sensor data, the sensor data from the three sensors are used to classify the temporal window as breathing disturbed or not.

In some embodiments, the system uses sensor data from at least one PPG sensor in classifying the temporal window as breathing disturbed or not. In some embodiments, the system does not use the sensor data generated by the green PPG sensor and instead calculates HRV from the sensor data generated by the red PPG sensor, and uses the calculated HRV to classify the temporal window as breathing disturbed or not. In some embodiments, the system uses the sensor data generated by the PPG sensor and not the sensor data generated by the red PPG sensor, the IR PPG sensor, or the accelerometer. In some cases, the system uses sensor data generated by a GSR sensor to classify the temporal window as breathing disturbed or not and/or to generate a breathing disturbance score.

In some embodiments, upon determining that a first condition is satisfied, the system uses sensor data from a first combination of sensors, and upon determining that the first condition is not satisfied, the system uses sensor data from a second combination of sensors different from the first combination of sensors. For example, in some cases, if the wearable device determines that the optical signal quality is poor from the red and infrared PPG sensors, the wearable device does not extract features from the red and infrared PPG data and extracts features (e.g., heart rate information or other indicators) only from the green sensor data. Alternatively or additionally, the wearable device may turn off the red and infrared PPG sensors upon determining that the optical signal quality is poor from the red and infrared PPG sensors (e.g., to conserve power and/or computing resources). Although the red and infrared PPG sensors are used as examples, the techniques described herein can be extended to any of the sensors or any combination thereof In some embodiments, upon determining that a second condition is satisfied, the system uses a first classification rule for classifying the temporal window as breathing disturbed or not, and upon determining that the second condition is not satisfied, the system uses a second classification rule different from the first classification rule for classifying the temporal window as breathing disturbed or not. In some cases, the wearable device may activate or deactivate one or more sensors based on the sensor data. For example, upon determining that the accelerometer data indicates that the user has been moving around for the past minute (or 5, 15, or 30 minutes, for example), the wearable device may turn off one or more sensors that are used for generating sleep metrics (e.g., including breathing disturbance scores/metrics). In some cases, upon determining that the accelerometer data indicates that the user has been moving around for the past minute (or 5, 15, or 30 minutes, for example), the wearable device deactivates one or more red PPG sensors and one or more infrared PPG sensors. The wearable device may activate one or more deactivated sensors based on a determination that the user may be sleeping (e.g., based on a determination that the accelerometer data indicates that the user has not been moving around for the past minute (or 5, 15, or 30 minutes, for example).

Although one minute is used herein as an example temporal window for which this classification can occur, other temporal windows having a different duration may be used (e.g., 30 second temporal windows, 5-minute temporal windows, etc.). In one embodiment, each temporal window has a fixed duration. In another embodiment, the duration of the temporal window is adjusted over time based on the user's sleeping or breathing patterns. For example, if the system (e.g., any combination of the wearable device 100, the client device 170, and the server 175) determines that the user's breathing disturbances frequently extend across multiple temporal windows, the duration of the temporal windows may be increased.

In some embodiments, the system may automatically detect blocks of time during which the user of the wearable device 100 is (or was) asleep. Here, automatic detection may refer to a detection that occurs without an explicit instruction from the user, such as traversing on-screen menus or otherwise inputting periods of time where the user is sleeping. It is to be appreciated that the term "automatic" does not preclude a case where the user may enable such a feature or act in a way that does not represent an explicit instruction of the timing when the user transitions between different sleep states. Such an embodiment that detects blocks of time in which the user is (or was) asleep may obtain a set of features for one or more periods of time from motion data and/or PPG data obtained from a set of one or more motion sensors or data derived therefrom. The system may then classify the one or more periods of time as one of a plurality of statuses of the user based on the set of features determined for the one or more periods of time. The statuses may be indicative of relative degree of movement of the user. In some cases, the statuses may be enumerated state values, such as active or inactive, where each state represent a different degree of movement or likelihood that the user is in a sleep state. In some embodiments, only the motion data is used to detect the period during which the user is (or was) asleep. In other embodiments, sensor data from a combination of the motion sensor and one or more PPG sensors is used to detect the period during which the user is (or was) asleep.

Figure 4:
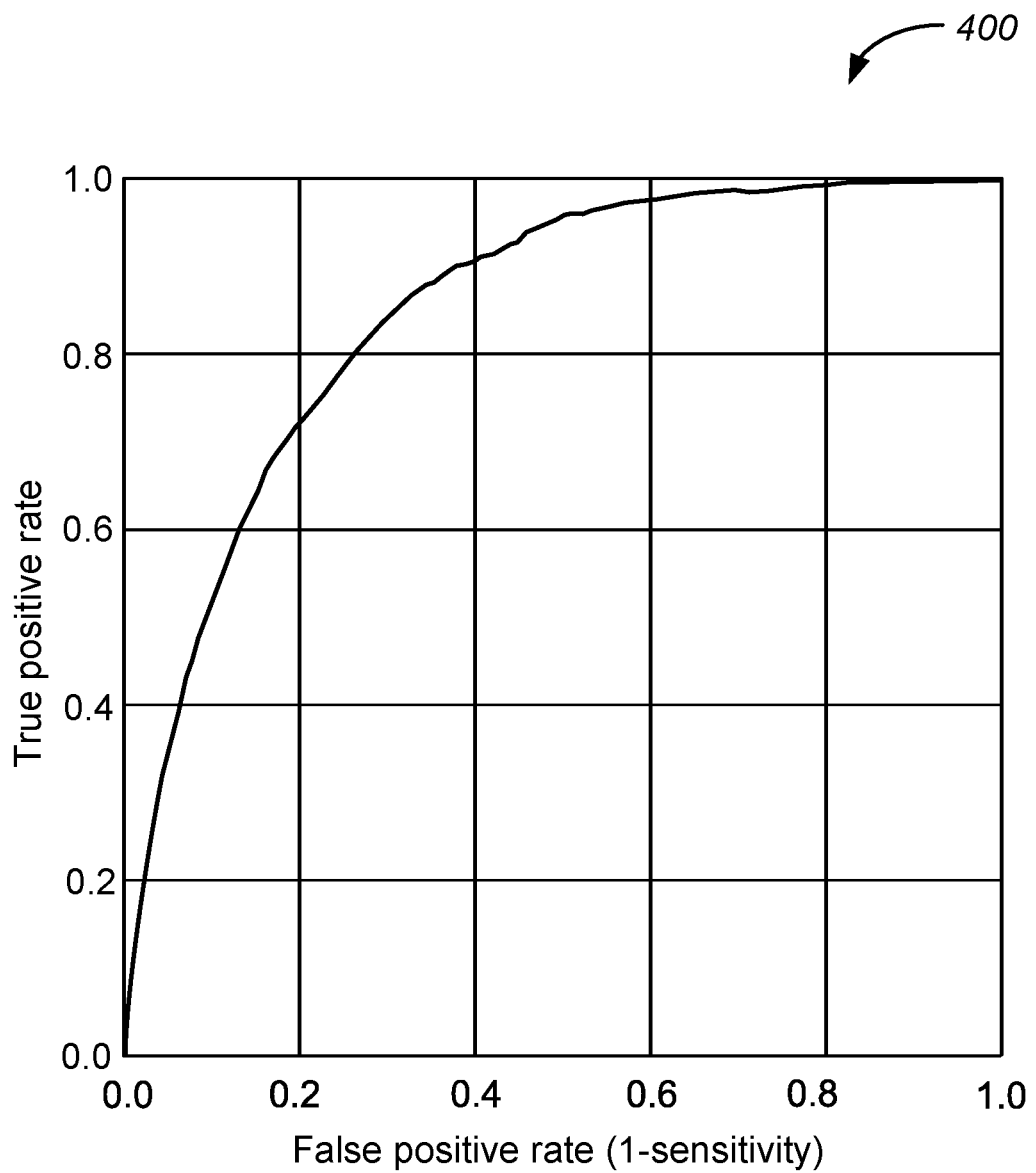
FIG. 4 illustrates a receiver operating characteristic (ROC) curve of a system in accordance with aspects of this disclosure.

The minute-by-minute performance of the classifier can be characterized by a receiver operating characteristic (ROC) curve. An example ROC curve 400 is shown in FIG. 4. The epoch (or temporal window) classifier outputs a probability of the minute being breathing disturbed. To make a decision about the minute, the system may apply a threshold such that if the output probability is above the threshold, the system declares the minute to be breathing disturbed, and otherwise, the system declares the minute to be normal (or not breathing disturbed). The value of this threshold is selected to tradeoff between false positives and missed detections. For instance, a low threshold would have few missed detections but may have many false positives. The determination of the probability of the temporal window being sleep disturbed may be based on demographic data.

For example, the indicators and/or features described herein may be weighted differently based on the demographic data associated with the user. The demographic data may include one or more of the user's body mass index (BMI), age, neck circumference, weight, height, gender, and the like. In some cases, the probability may be increased or decreased based on the demographic data associated with the user (e.g., based on whether the user belongs to a specific category of users more (or less) likely to experience breathing disturbances). For example, if the user is 65 years old (or greater), has a BMI of 35 (or greater), and has a neck circumference of 18 inches (or greater), the probability of a given temporal window being sleep disturbed may be increased (e.g., by adding an offset or multiplying by an offset). Alternatively or additionally, the threshold for determining whether a given temporal window is sleep disturbed or not may be increased or decreased based on the demographic data associated with the user (e.g., based on whether the user belongs to a specific category of users more (or less) likely to experience breathing disturbances). In some embodiments, the specific user categories are generated and/or updated based on the demographics data and the classifications/breathing scores gathered across a plurality of users.

The ROC curve of FIG. 4 captures this tradeoff by plotting the true positive rate (sensitivity) against the false positive rate (specificity) over a range of thresholds. The example of FIG. 4 illustrates the performance of a classification method based on PPG and accelerometer features over 8500 minutes of sleep across several people. In some implementations, since most subjects will not have breathing disturbances during sleep, the system selects or uses a threshold value corresponding to an operating point close to the vertical axis. This would in effect sacrifice sensitivity (true positives) for specificity. In some cases, the system adjusts the threshold value based on sensor data or other metrics generated over time and/or based on user input or feedback. In some cases, the threshold value is determined such that the false positive rate is fixed or is below a threshold level. In some cases, the threshold value is maintained and updated by a cloud service (e.g., server 175) and is downloaded (periodically or when the value is updated) by the client device 170 and/or the wearable device 100 from the cloud service.

In some embodiments, the sensor data from different sensors are weighted differently. For example, each sensor may be assigned a fixed weight indicative of how much the sensor is to contribute to the classification of the temporal windows as breathing disturbed or not. In another example, the weights assigned to the sensors are adjusted based on the sensor data (e.g., the sensor data from the red PPG sensor and the IR PPG sensor may be weighted more heavily based on the sensor data from the green PPG sensor remaining constant or not changing more than a threshold amount for a threshold period of time).

The labels for each temporal window (e.g., breathing disturbed or normal) are fed to a second classification algorithm to determine the severity of breathing disturbance for a given sleep period (e.g., the entire night). This second classification stage may combine information from the user's demographics (gender, weight, height, age) and the observed night of sleep in its entirety to assign a breathing disturbance score (e.g., severity of breathing disturbance) for the user's night of sleep. The system may determine the percentage of temporal windows that are classified as breathing disturbed and select a score based on the percentage. In some embodiments, the system generates a composite score for multiple nights, weeks, months, and/or years.

For example, the threshold number of nights needed before the system generates the composite score may differ based on the signal quality of the one or more sensors. For example, if the signal quality of one or more sensors has been poor for the nights, the system generates the composite score after collecting more than 4 nights' worth of sensor data, classifications, and/or breathing disturbance scores. On the other hand, if the signal quality of one or more sensors has been good, the system generates the composite score after collecting more than 2 nights' worth of sensor data, classifications, and/or breathing disturbance scores.

In one example, the breathing disturbance score is one of normal (e.g., below 5%), mild (e.g., 5-10%), moderate (e.g., 10-20%), or severe (e.g., 20% or above). In another example, breathing disturbance score is one of normal (e.g., below 5%) or not normal (e.g., 5% or above). Such information in some embodiments may also be used to provide a sleep fitness score, where higher breathing disturbance scores can correlate with lower sleep fitness scores, along with data such as motion data determined using an accelerometer and the like. For example, a night with a normal breathing disturbance score and a within a normal range of motion for a user might receive a "normal" sleep fitness score, while a night with a not normal breathing disturbance score or higher than normal amount of motion might receive a "not normal" sleep fitness score, using combinations of factors discussed herein as would be apparent to one or ordinary skill in the art in light of the teachings and suggestions contained herein. Further, although example percentage ranges are used in various examples, the percentage ranges may be set to other values and may be adjusted based on other historical data and/or physiological metrics of the user and/or other users. In some embodiments, the system generates the breathing disturbance score only if the sleep period exceeds a threshold amount of time (e.g., 2, 3, 4 hours). In some cases, the threshold amount of time may be adjusted based on the signal quality of the one or more sensors. For example, if the signal quality of one or more sensors is poor, the system generates the breathing disturbance score only if the sleep period exceeds four hours, and if the signal quality of one or more sensors is good, the system generates the breathing disturbance score as long as the sleep period exceeds two hours. Alternatively, the system generates the breathing disturbance score regardless of how long the sleep period is. In some embodiments, the determination of the breathing disturbance score may be based on demographic data. For example, the percentage of the temporal windows classified as breathing disturbed may be increased or decreased based on the demographic data associated with the user (e.g., based on whether the user belongs to a specific category of users more (or less) likely to experience breathing disturbances). The demographic data may include one or more of the user's body mass index (BMI), age, neck circumference, weight, height, gender, and the like. For example, if the user is 65 years old (or greater), has a BMI of 35 (or greater), and has a neck circumference of 18 inches (or greater), the percentage of the temporal windows classified as breathing disturbed may be increased (e.g., by adding an offset or multiplying by an offset). The specific user categories can be generated and/or updated based on the demographics data and the classifications/breathing scores gathered across a plurality of users. For example, if the system determines that a fewer number of users between age 65 and age 67 are experiencing breathing disturbances, the example above may be updated so that users of age 68 and older having a BMI of 35 or greater, and having a neck circumference of 18 inches or greater would have their breathing disturbance score adjusted upward (or have their probabilities of individual temporal windows being sleep disturbed adjusted upward).

In some embodiments, the system outputs one or more additional breathing disturbance metrics. For example, the system may output one or more of the percentage of temporal windows classified as being breathing disturbed, the number of breathing disturbances per hour (or per night), the apnea-hypopnea index (AHI), and a sleep apnea severity score (e.g., normal for AHI below 5, mild for AHI of 5 or greater and below 15, moderate for AHI of 15 or greater and below 30, and severe for AHI of 30 or above). The system may also output a graph illustrating the trend in the breathing disturbance scores or metrics of the user over time (e.g., daily, weekly, monthly, and/or yearly). In some embodiments, the system may output a recommendation that the user schedule a visit to a doctor.

In some implementations, upon determining that the breathing disturbance score or metric is not normal (e.g., above a threshold percentage of temporal windows classified as breathing disturbed or above a threshold number of apnea events per hour), the system outputs a question along with a selectable option to gather additional information from the user. For example, the client device 170 may display the question "Are you drowsy all the time?" with a user interface element for indicating "yes" or "no." Upon detecting user selection of a predetermined option (e.g., "yes"), the system outputs a recommendation for a sleep laboratory or a doctor for further examination. The system may select the sleep laboratory or doctor from a list of sleep laboratories and/or doctors registered (e.g., as part of a revenue share program with the company implementing the system) and also in the user's geographical area. In some cases, upon determining that the breathing disturbance score or metric is not normal (e.g., above a threshold percentage of temporal windows classified as breathing disturbed or above a threshold number of apnea events per hour), the system outputs the breathing disturbance score or metric for presentation to the user along with an advertisement for a sleep laboratory, doctor, or medical device company (e.g., a continuous positive airway pressure (CPAP) machine manufactured by a medical device company).

In some embodiments, the breathing disturbance scores generated for a given user are stored in cloud storage and accessible to the user so that the user can monitor the degree to which the user is experiencing breathing disturbances over time and see how the user compares to other users of similar demographics (e.g., age, gender, height, weight, activity level, etc.). Both the user's own breathing disturbance scores and the benchmarking data generated based on other users' breathing disturbance scores will enable the user to work to decrease the severity of breathing disturbances though practices including CPAP therapy, weight loss, and/or changing sleeping orientation.

In some embodiments, upon determining that the user's breathing disturbance score for a given night is one of mild, moderate, or severe, the system accesses the past scores stored in the cloud or on the user's mobile device and determines whether the user's breathing disturbance score for the given night is unusual. For example, if the user's never had a score other than "normal" for the past 3 years, the system may ignore the score of "severe" generated for last night (e.g., once, twice, or for a threshold number of times) and output a score of "normal." Alternatively, in such a case, the system may adjust the score down to "mild" or "moderate."

In some embodiments, the breathing disturbance score or other breathing or sleep-related score, is presented in a graphical user interface (GUI) that also includes the benchmarking data generated based on other users' breathing disturbance scores. In some embodiments, the breathing disturbance score is presented in a GUI that also includes the user's weight, the user's activity level during the daytime, and/or the user's sleeping orientation. In some embodiments, the breathing disturbance score is presented in a GUI that also includes the history of the user's breathing disturbance scores/metrics. In some of such embodiments, the history spans at least 30 days. In some cases, the history spans at least 365 days.

In some embodiments, the wearable device 100 includes a pressure sensor configured to sense relative motion of the wearable device with respect to the user's skin. For example, the pressure sensor generates sensor data indicative of how much force is exerted on the wearable device 100 in a direction perpendicular to the user's skin (e.g., force pushing the wearable device 100 into the user's wrist) and/or in a direction parallel to the user's skin (e.g., force pushing the wearable device 100 up and down the user's wrist and/or along the circumference of the user's wrist).

In some embodiments, upon determining that a temporal window that would otherwise be classified as breathing disturbed includes pressure sensor data indicating that the force exerted in a direction perpendicular to the user's skin is greater than a threshold level, the system classifies the temporal window as normal (or not breathing disturbed). In some embodiments, upon determining that a temporal window that would otherwise be classified as breathing disturbed includes pressure sensor data indicating that the force exerted in a direction parallel to the axis of the user's forearm is greater than a threshold level, the system classifies the temporal window as normal (or not breathing disturbed). In some embodiments, upon determining that a temporal window that would otherwise be classified as breathing disturbed includes pressure sensor data indicating that the force exerted in a direction parallel to the tangential direction of the user's wrist is greater than a threshold level, the system classifies the temporal window as normal (or not breathing disturbed).

In some embodiments, upon determining that the pressure sensor data generated during a given time period indicates that the force exerted in a direction perpendicular to the user's skin is greater than a threshold level, the system ignores other sensor data (e.g., PPG sensor data and/or motion sensor data) generated during the given time period in classifying the temporal windows as breathing disturbed or not. In some embodiments, upon determining that the pressure sensor data generated during a given time period indicates that the force exerted in a direction parallel to the axis of the user's forearm is greater than a threshold level, the system ignores other sensor data (e.g., PPG sensor data and/or motion sensor data) generated during the given time period in classifying the temporal windows as breathing disturbed or not. In some embodiments, upon determining that the pressure sensor data generated during a given time period indicates that the force exerted in a direction parallel to the tangential direction of the user's wrist is greater than a threshold level, the system ignores other sensor data (e.g., PPG sensor data and/or motion sensor data) generated during the given time period in classifying the temporal windows as breathing disturbed or not.

In one embodiment, the wearable device performs all the processing and sends the result (e.g., classifications and breathing disturbance score) to the mobile device or the centralized server. In another embodiment, the wearable device determines the classifications but the mobile device or server determines the breathing disturbance score. In yet another embodiment, a portion of the processing is performed on the wearable device, and the remaining portion of the processing can be performed on the mobile device or server. In yet another embodiment, the sensor data is sent to the mobile device or server without any processing. In some of such embodiments, the sensor data is processed by the mobile device or server to determine the classifications and the breathing disturbance score.

In some embodiments, the detection of breathing disturbances occurs on a mobile device (e.g., the client device 170) that can communicate with the wearable device. For example, the sensor data collected by the wearable device may be sent (with or without additional processing by the wearable device) to such a mobile device of the user, and the mobile device can analyze the sensor data to classify the individual temporal windows and generate a breathing disturbance score. The mobile device may wirelessly transmit the classifications and/or the breathing disturbance scores or metrics to a cloud service (e.g., the server 175) for storage.

Advantageously, detection of breathing disturbances on such a mobile device can provide the power savings for the wearable device (e.g., since detection is not performed by the wearable device), without requiring the infrastructure of a centralized database.

In some embodiments, the detection of breathing disturbances occurs on a centralized server (e.g., the server 175) that can communicate with the wearable device and/or the mobile device associated with the user. For example, the sensor data collected by the wearable device may be sent (with or without additional processing by the wearable device) to such a server (either directly or via the mobile device), and the server can analyze the sensor data to classify the individual temporal windows and generate a breathing disturbance score. The centralized server may wireless transmit the classifications and the breathing disturbance scores or metrics to the mobile device and/or the wearable device for storage and presentation to the user.

Advantageously, detection of breathing disturbances on such a centralized server can provide the power savings for the wearable device (e.g., since detection is not performed by the wearable device) and more robust detection since more data and processing power may be available on the server compared to the client device 170.

Figure 5:
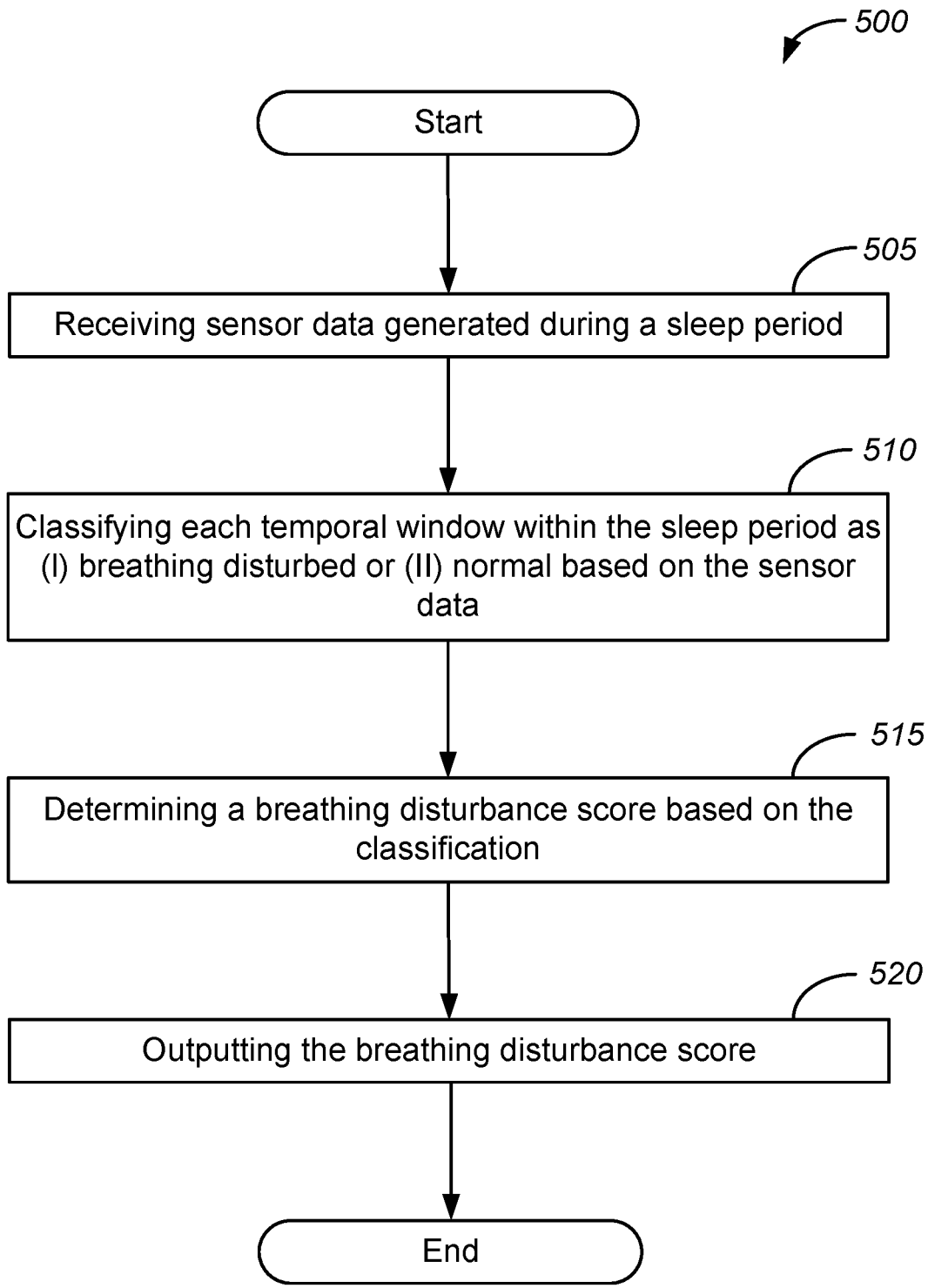
FIG. 5 illustrates an example method of monitoring breathing disturbances in accordance with aspects of this disclosure.

FIG. 5 is a flowchart illustrating an example method for monitoring breathing disturbances of a user in accordance with aspects of this disclosure. The method 500 may be performed by the wearable device 100, the client device 170, and/or the server 175, either alone or in a distributed manner. The method 500 illustrates an example algorithm that may be programmed, using any suitable programming environment or language, to create machine code capable of execution by a CPU or microcontroller of the wearable device 100, the client device 170, and/or the server 175. Various embodiments may be coded using assembly, C, OBJECTIVE-C, C++, JAVA, or other human-readable languages and then compiled, assembled, or otherwise transformed into machine code that can be loaded into read-only memory (ROM), erasable programmable read-only memory (EPROM), or other recordable memory of the wearable device 100, the client device 170, and/or the server 175 that is coupled to the CPU or microcontroller and then then executed by the CPU or microcontroller.

At block 505, the system receives sensor data generated by one or more sensors of the wearable device 100 worn by the user, wherein the sensor data is generated during a first period (e.g., a sleep period during which the user is or was sleeping). The sensor data may include sensor data generated by any combination of the sensors described herein (or other data generated based on such sensor data). For example, the sensor data may include green PPG data generated by the green PPG sensor 166, red PPG data generated by the red PPG sensor 167, IR PPG data generated by the IR PPG sensor 168, and/or motion data generated by the accelerometer 161 (or other motion sensor described herein). As described herein, the sensor data may be generated by one or more sensors provided on the wearable device 100 and/or one or more additional sensors external to the wearable device 100.

At block 510, the system, for each respective temporal window of a plurality of temporal windows within the first period, classifies the respective temporal window as one of (i) breathing disturbed or (ii) not breathing disturbed, based on the sensor data generated during the respective temporal window. For example, the temporal windows may each be 1-minute long, and the system, for each respective minute of a plurality of minutes within the sleep period, may analyze the sensor data generated by each of the sensors (e.g., one or more motion and PPG sensors) during that minute and determine whether the user is likely to have been experiencing breathing disturbances during that minute. In another example, the temporal window is one of 30 seconds, 2 minutes, or 5 minutes. The system may classify a given minute based on whether one or more of the received sensor streams (e.g., each sensor stream generated by one of the sensors provided on the wearable activity tracker) include a feature indicative of the user having a breathing disturbance. For example, upon determining that the green PPG sensor data generated by a green PPG sensor of the wearable activity tracker includes a first period of slow oscillations followed a second period of rapid oscillations during a given minute, the system may classify the given minute as breathing disturbed. The system may determine the likelihood that the user is (or was) having a breathing disturbance during the given minute based on the similarity between the features extracted from the sensor streams and one or more predetermined features indicative of user having a breathing disturbance, and classify the given minute as breathing disturbed if the likelihood exceeds a threshold (e.g., 30%, 50%, 75%, etc. as illustrated by the ROC curve of FIG. 4). If multiple sensor streams during the given minute include features similar to the one or more predetermined features indicative of user having a breathing disturbance, the likelihood of the user having a breathing disturbance during the given minute may be higher. In some embodiments, prior to classifying the temporal windows, the system may first determine a specific period during which the user is (or was) asleep, and classify each temporal window within the specific period, where the specific period is a subset of the first period for which the sensor data was received at block 505. In other embodiments, the system classifies each temporal window within the first period without determining whether the user is (or was) asleep during any portion of the first period. In some implementations, the system may utilize information gathered outside the first period (or the specific period during which the user is determined to have been asleep). For example, the determination of whether a temporal window is breathing disturbed or not may be based on the user's age, gender, height, weight, activity level, and/or other factors. In another example, the system determines a baseline heart rate (or other physiological metric such as SpO2, heart rate variability, respiration rate, etc.) associated with the user based on the user's heart rate measured throughout the day (e.g., outside the period during which the user is determined to have been asleep) or the user's heart rate over a number of days, weeks, months, or years, and uses the baseline heart rate (or other physiological metrics) to determine whether a given temporal window should be classified as breathing disturbed or not. For example, a spike in heart rate of 105 may be indicative of a breathing disturbance for a user whose baseline heartrate is 50, but may not be indicative of a breathing disturbance for another user whose baseline heartrate is 100.

At block 515, the system determines a breathing disturbance score based on the classification of the plurality of temporal windows. For example, the system determines the percentage of temporal windows that were classified as breathing disturbed and generates the breathing disturbance score based on the percentage. For example, the system may select the score from a set of available scores each associated with a percentage range (e.g., "normal" associated with a percentage range of 0-5, "mild" associated with a percentage range of 5-10, "moderate" associated with a percentage range of 10-20, and "severe" associated with a percentage range of 20+). In some embodiments, the system may determine the breathing disturbance score based on the classification and the information gathered outside the first period (or the specific period during which the user is determined to have been asleep). For example, the determination of the user's breathing disturbance score may be based on the user's age, gender, height, weight, activity level, and/or other factors.

At block 520, the system outputs the breathing disturbance score for presentation to the user. For example, the client device 170 may display the breathing disturbance score on the display screen of the client device 170 along with a benchmark breathing disturbance score generated based on other users similar to the user. Such a benchmark breathing disturbance score may be downloaded from the server 175. Additionally or alternatively, the client device 170 may receive a plurality of past breathing disturbance scores associated with the user from the cloud service storing such past breathing disturbance scores, and display a history of breathing disturbance scores on the display screen of the client device 170 based on the plurality of past breathing disturbance scores received from the cloud service. For example, the history may include a graph illustrating a trend in the breathing disturbance scores of the user. In some cases, additionally or alternatively, the system may transmit the breathing disturbance score to another device for display on said another device.

In the method 500, one or more of the blocks shown in FIG. 5 may be removed (e.g., not performed) and/or the order in which the method is performed may be switched. For example, in some embodiments, one or more of blocks 505, 510, 515 and 520 may be omitted. In some embodiments, additional blocks may be added to the method 500. The method 500 may be performed by the wearable device 100, the client device 170, and/or the server 175, either alone or in a distributed manner. For example, blocks 505 and 510 may be performed by the client device 170 and blocks 515 and 520 may be performed by the server 175. Alternatively, all of blocks 505-520 may be performed by the server 175 such that the server 175 receives the sensor data from the wearable device 100 or the client device 170 at block 505 and outputs the breathing disturbance score to the wearable device 100 or the client device 170 at block 520. The embodiments of the present disclosure are not limited to or by the example shown in FIG. 5, and other variations may be implemented without departing from the spirit of this disclosure.

Figure 6:
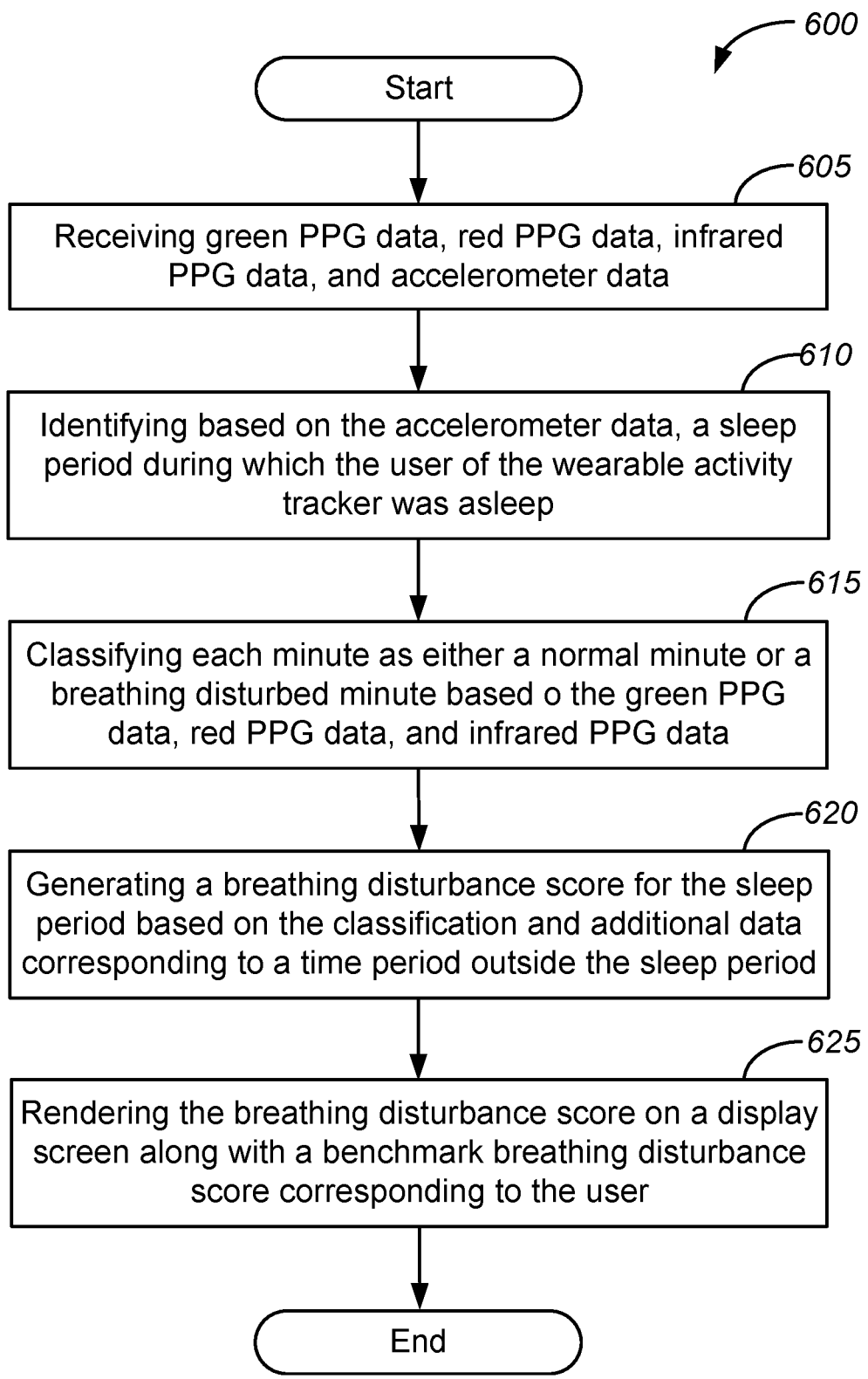
FIG. 6 illustrates another example method of monitoring breathing disturbances in accordance with aspects of this disclosure.

FIG. 6 is a flowchart illustrating an example method for monitoring breathing disturbances of a user in accordance with aspects of this disclosure. The method 600 may be performed by the wearable device 100, the client device 170, and/or the server 175, either alone or in a distributed manner. The method 600 illustrates an example algorithm that may be programmed, using any suitable programming environment or language, to create machine code capable of execution by a CPU or microcontroller of the wearable device 100, the client device 170, and/or the server 175. Various embodiments may be coded using assembly, C, OBJECTIVE-C, C++, JAVA, or other human-readable languages and then compiled, assembled, or otherwise transformed into machine code that can be loaded into read-only memory (ROM), erasable programmable read-only memory (EPROM), or other recordable memory of the wearable device 100, the client device 170, and/or the server 175 that is coupled to the CPU or microcontroller and then then executed by the CPU or microcontroller. For convenience, method 600 is described below as being performed by a server.

At block 605, the server receives first PPG data generated by at least one green PPG sensor, second PPG data generated by at least one red PPG sensor, third PPG data generated by at least one infrared PPG sensor, and accelerometer data generated by at least one accelerometer. Although accelerometer data is used in the example of FIG. 6, sensor data generated by one or more other motion sensors described herein may be used additionally or alternatively. In some embodiments, the server receives the data from the wearable device.

Alternatively, a mobile device receives the data from the wearable device (e.g., via Bluetooth or other wireless technologies), and the mobile device wirelessly transmits the data to the server. Each of the at least one green PPG sensor, the at least one red PPG sensor, the at least one infrared PPG sensor, and the at least one accelerometer may be provided on a single wearable activity tracker configured to be worn on a wrist of a user. In some embodiments, the PPG data and/or the accelerometer data may be raw data generated by the respective sensors. In other embodiments, the PPG data and/or the accelerometer data may be processed data generated by the wearable activity tracker based on such raw data. For example, the processed data may include a set of features extracted from one or more of the first, second, and third PPG data and accelerometer data (e.g., 17 features extracted from each minute's worth of sensor data). The set of features may be generated for individual temporal windows (e.g., for every minute of the sensor data, for every 5 minutes of the sensor data, etc.). In some embodiments, the sensors are provided on the wearable activity tracker such that each of the sensors are located on the same side of the user's wrist when the wearable activity tracker is worn on the user's wrist. In some embodiments, at least one sensor is not located on the same side of the user's wrist as the remaining sensors. In some cases, one or more sensors external to the wearable activity tracker are in communication with the mobile device and/or the server and wirelessly transmit additional sensor data to the mobile device and/or the server. For example, the mobile device may communicate with a bed sensor to collect ballistocardiogram data indicative of the ballistic forces on the heart. In some cases, respiration data may be generated based on one or more of the first PPG data, the second PPG data, the third PPG data, the accelerometer data, and/or the ballistocardiogram data.

At block 610, the server identifies, based on the accelerometer data (or a portion or subset of the set of features extracted from the accelerometer data), a sleep period during which the user of the wearable activity tracker was asleep. In some embodiments, the server identifies the sleep period by determining which portion of the accelerometer data indicates movement of the user that is consistent with the user sleeping. For example, the server may identify the sleep period by determining which portion of the accelerometer data (or one or more features associated with which timestamp or temporal window) is indicative of movement that is less than a threshold level, and determining the time period during which such portion of the accelerometer data was generated as the sleep period. In some cases, the server identifies the sleep period based on a determination that the portion of the accelerometer data that corresponds to the sleep period does not indicate a threshold level of movement for at least a threshold amount of time. Even when the user wearing the wearable activity tracker is sleeping, the wearable activity tracker may experience some movement and the accelerometer data may reflect such movement. In some embodiments, such movement while the user is sleeping is ignored by the server, and the period during which such movement occurs is not excluded from the sleep period.

At block 615, the server classifies each minute of a plurality of minutes within the sleep period as one of (i) a normal minute, or (ii) a breathing disturbed minute. The server may classify the individual minutes based on (i) the portion of the green PPG data generated during the sleep period, (ii) the portion of the red PPG data generated during the sleep period, (iii) the portion of the infrared PPG data generated during the sleep period, and any combination thereof (or a subset of the set of features extracted from the green PPG data, the red PPG data, and/or the infrared PPG data, for example, 5 features extracted from the green PPG data generated during the given minute, and 8 features extracted from the combination of the red PPG data and the infrared PPG data generated during the given minute). The server may classify the individual minutes further based on additional data corresponding to a time period outside the sleep period. For example, the determination of whether a minute is breathing disturbed or not may be based on the user's age, gender, height, weight, activity level, and/or other factors. In another example, the server determines a baseline heart rate (or other physiological metric such as $SpO_2$, heart rate variability, respiration rate, etc.) associated with the user based on the user's heart rate measured throughout the day (e.g., outside the period during which the user is determined to have been asleep) or the user's heart rate over a number of days, weeks, months, or years, and uses the baseline heart rate (or other physiological metrics) to determine whether a given minute should be classified as breathing disturbed or not. For example, a spike in heart rate of 105 may be indicative of a breathing disturbance for a user whose baseline heartrate is 50, but may not be indicative of a breathing disturbance for another user whose baseline heartrate is 100. In some embodiments, the server generates respiration data based on one or more of the first PPG data, the second PPG data, the third PPG data, the accelerometer data, and/or the ballistocardiogram data, and classifies the individual minutes based on the respiration data. For example, the server may classify a given minute as breathing disturbed based on a determination that a portion of the respiration data corresponding to the given minute includes a pattern of low values followed by a spike in value In some embodiments, the server classifies the individual minutes within a period during which the sensor data indicates movement less than a threshold level and does not classify the individual minutes within another period during which the sensor data indicates movement greater than the threshold level. In some embodiments, the server classifies a given minute based on a determination that the given minute is associated movement less than a threshold level. For example, the server may first determine that the given minute is associated movement less than a threshold level prior to classifying the given minute.

At block 620, the server generates a breathing disturbance score for the sleep period based on the classification of the individual minutes. For example, the server determines the percentage of minutes that were classified as breathing disturbed and generates the breathing disturbance score based on the percentage. For example, the server may select the score from a set of available scores each associated with a percentage range (e.g., "normal" associated with a percentage range of 0-5, "mild" associated with a percentage range of 5-10, "moderate" associated with a percentage range of 10-20, and "severe" associated with a percentage range of 20+). In some embodiments, the server may determine the breathing disturbance score based on the classification and the information gathered outside the sleep period (or the specific period during which the user is determined to have been asleep). For example, the determination of the user's breathing disturbance score may be based on the user's age, gender, height, weight, activity level, and/or other factors. The server may update the benchmark breathing disturbance score corresponding to the user's age, gender, height, weight, activity level, and/or other categories, based on the breathing disturbance score of the user. The server may maintain past breathing disturbance scores for a plurality of users each associated with respective wearable activity trackers.

At block 625, the server causes the breathing disturbance score to be rendered on a display screen of the mobile device. For example, the server may wirelessly transmit the breathing disturbance score to the mobile device, and the mobile device may display the breathing disturbance score along with a benchmark breathing disturbance score corresponding to the user's age, gender, height, weight, activity level, and/or other categories. Such a benchmark breathing disturbance score may be downloaded from the server or another service. For example, the mobile device may request from the server a benchmark breathing disturbance score associated with a user category to which the user belongs (e.g., any combination of user attributes such as "30-39 years old, male, 6'0"-6'3", 175-185 lbs"), and the server may wirelessly transmit the benchmark breathing disturbance score associated with the user category. In some embodiments, how the individual minutes are classified (e.g., as breathing disturbed or normal) is displayed in a user display. In one example, such user interface does not include any classifications of individual minutes outside the sleep period. In another example, such user interface may include classifications of individual minutes outside the sleep period.

In the method 600, one or more of the blocks shown in FIG. 6 may be removed (e.g., not performed) and/or the order in which the method is performed may be switched. For example, in some embodiments, one or more of blocks 605, 610, 615, 620, and 625 may be omitted. In some embodiments, additional blocks may be added to the method 600. The method 600 may be performed by the wearable device 100, the client device 170, and/or the server 175, either alone or in a distributed manner. As one example, blocks 605 and 610 may be performed by the wearable device 100 or the client device 170, blocks 615 and 620 may be performed by the server 175, and block 625 may be performed by the client device 170. For example, by performing at least some of the processing on the wearable device 100, the amount of data that needs to be wirelessly transmitted from the wearable device 100 to the client device 170 and/or the server 175 can be reduced, thereby reducing the bandwidth requirements and/or reducing the latency associated with data transfer/sync. Alternatively, all of blocks 605-625 may be performed by the wearable device 100 alone, the client device 170 alone, or the server 175 alone. For example, by performing at least some of the processing on the server 175, the amount of processing that needs to be performed by the client device 170 can be reduced, thereby reducing power consumption and/or computing resource consumption on the client device 170. In some embodiments, no calculation for classifying the temporal windows and/or generating the breathing disturbance score is performed by the client device 170. In other embodiments, at least some of the calculation for classifying the temporal windows and/or generating the breathing disturbance score is performed by the client device 170. The embodiments of the present disclosure are not limited to or by the example shown in FIG. 6, and other variations may be implemented without departing from the spirit of this disclosure.

Figure 7:
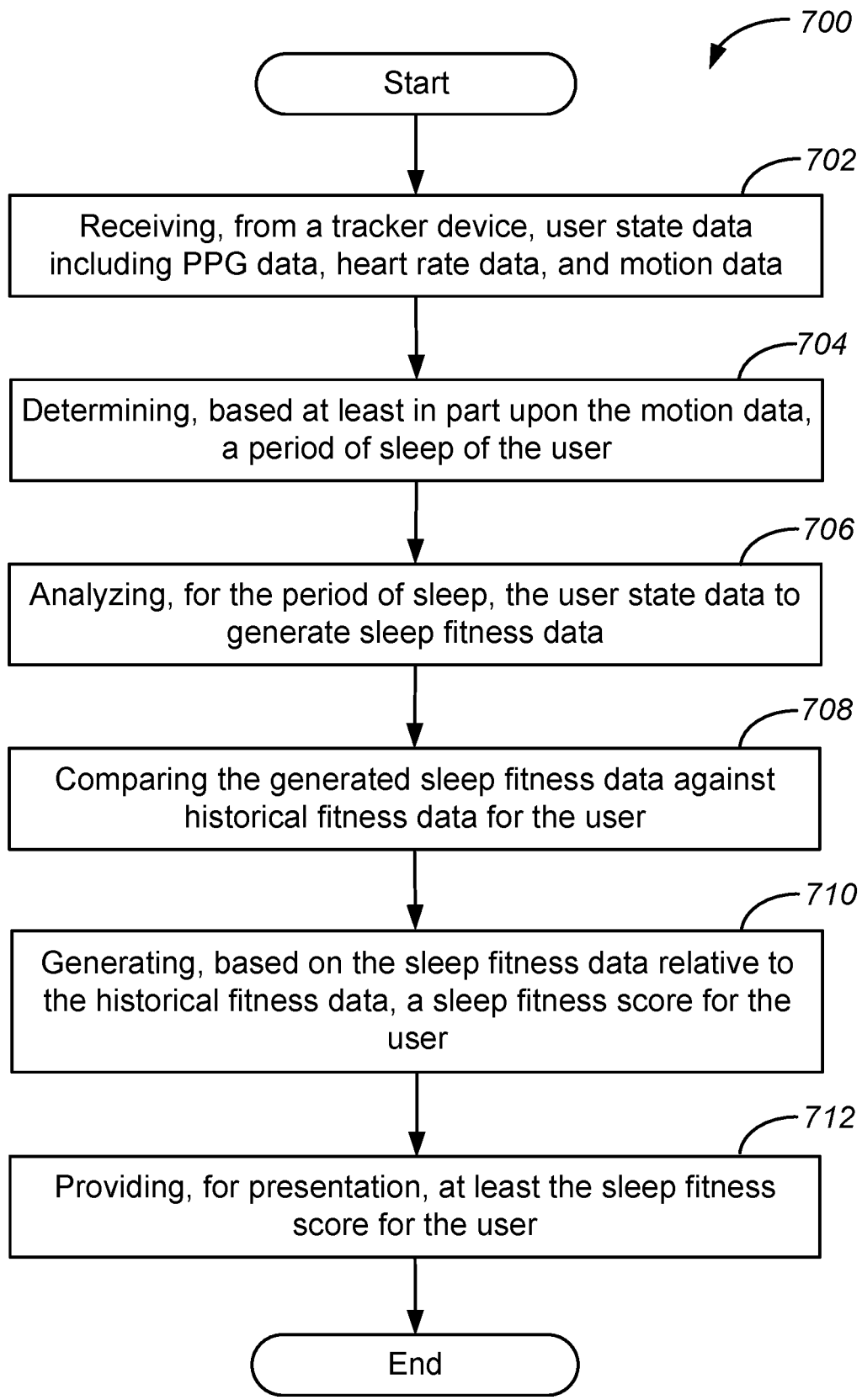
FIG. 7 illustrates an example method of determining a fitness score in accordance with aspects of this disclosure.

FIG. 7 is a flowchart illustrating an example method for generating a sleep fitness score for a user in accordance with aspects of this disclosure. The method 700 may be performed by the wearable device 100, the client device 170, and/or the server 175, among other such devices, alone or in a distributed manner. At block 702, user state data is received from a tracker device, although as mentioned in some embodiments the data can be received from one or more sensors, or other such sources, to a sub-system on the tracker device. In this example the user state data includes PPG data, heart rate data, and motion rate data, although various other types of data may be received as well, as may include blood pressure data, eye movement data, audio data, ballistocardiogram data, body temperature data, and brain activity data, among other such options. As mentioned, this data can be obtained using appropriate sensors or mechanisms on, or in communication with, the tracker in at least some embodiments. Any appropriate information regarding the health, fitness, or state of the user may be obtained within the scope of the various embodiments.

Once obtained, at block 704 the process determines at least one period of sleep of the user. This can be determined as discussed elsewhere herein, as may use motion data in combination with any other relevant user state data. The motion data can be obtained from an accelerometer or other motion sensor on the device, or from a camera or image sensor, among other such options. Also as mentioned, this can include determining multiple windows or periods of sleep over a night or specified time period in some embodiments. For at least one period of sleep, at block 706 the user state data is analyzed to generate sleep fitness data. As discussed elsewhere herein, this can involve using any of the user state data to generate data useful for determining sleep fitness, as may involve determining a breathing disturbance score using the PPG data, a restlessness score using the motion data, a pulse regularity score using the heart rate information, etc. Any data useful in determining a sleep state or fitness of the user may be calculated as discussed and suggested herein, and as would be apparent to one of ordinary skill in the art in light of the present disclosure. At block 708 at least some of the generated or calculated sleep fitness data can be compared against historical sleep fitness data. As mentioned, this can be used to determine whether any of the values deviate from those typically determined for a user, as different users will have different amounts of motion or state variation during normal sleep patterns for those users. At block 710 a sleep fitness score can be generated for that user for the respective time period. As mentioned, this can be based upon any or all of the sleep fitness data, as well as any variance from the historical values. For example, all normal values being determined that correspond to historical averages for a given user, within an allowable variance range or threshold, might result in a normal fitness score being calculated for a user. This might result in a score of "normal," 100% for fit, etc. In some embodiments a weighted function of sleep fitness data can be used to generate a sleep fitness score, such as from 0 to 100, which can be presented to a user, with a separate indication of whether this score is normal for that user. If the score is outside a normal range, the score and indication may be accompanied by additional information, such as may relate to the types of data that resulted in the atypical score. The weightings of the various parameters of the function can be determined experimentally or through use of a trained machine learning algorithm, among other such options. In some embodiments the sleep fitness score may be a simple score of "fit" or "unfit," among other such options, where any individual user state data outside the normal range may result in an unfit score. In various embodiments a sleep fitness score may be related to a single sleep fitness data point, such as may relate to a breathing disturbance score or a restlessness score determined based on at least detected motion, while in various embodiments combinations of the factors discussed and suggested herein are utilized to provide a more accurate and useful determination. Once generated, at block 712 the process can provide at least the sleep fitness score for presentation, and may also provide other relevant information as discussed and suggested herein.

Traditional sleep analysis devices (those used by sleep labs or sensor systems such as ARES™ Home Sleep Test), while more accurate, are only used by individuals who already know or suspect they have sleep disorders. One advantage of using sensors on a wearable activity tracker is that sleep quality can be monitored for any individual for months and years without disrupting his or her natural sleep routine. A combination of wrist-worn sensors coupled with machine learning algorithms can provide information relevant to sleep quality. Data from these different sensor streams are extracted using novel feature extraction algorithms.

Sleep apnea diagnosis typically requires the equipment and personnel of a sleep lab. A sleep technician monitors the subject while they sleep and records data from an array of sensors, such as, for example, brain activity electroencephalogram (EEG) measurements, $SpO_2$ via PPG measurements, airflow via nasal tube and pressure transducer measurements, and/or electrical monitoring of heartbeats (ECG). In some implementations, a finger $SpO_2$ sensor coupled with an accelerometer and respiration derived from a bed sensor can be used to monitor breathing disturbances of a user. In other implementations, a wearable platform that records $SpO_2$ and heart rate through a forehead reflectance pulse oximeter and respiratory effort though a nasal pressure sensor may be used. These implementations may be expensive due to the equipment required, the operation of which may not easily be available to the layperson. Further, these implementations may require manual scoring of the data in order to come up with a medical diagnosis. Hence, a mass screening system implemented using an everyday wearable activity tracker would enable people to determine whether they should seek further medical care with minimal cost compared to a sleep lab and without disrupting their natural sleep routine.

In some embodiments, the wearable device 100 is designed to be worn every day and is configured to provide, in addition to sleep metrics, other metrics or notifications (e.g., smartphone notifications, step count, jogging statistics, etc.). In such cases, the wearable device 100 is therefore much more likely to be acquired by users who do not suspect they have sleep apnea or other sleep/breathing conditions, and provides valuable diagnostic information to the large number of users who do not yet know they have sleep apnea or other sleep/breathing conditions.

Information and signals disclosed herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof The various illustrative logical blocks, and algorithm steps described in connection with the embodiments disclosed herein may be implemented as electronic hardware, computer software, or combinations of both. To clearly illustrate this interchangeability of hardware and software, various illustrative components, blocks, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The techniques described herein may be implemented in hardware, software, firmware, or any combination thereof. Such techniques may be implemented in any of a variety of devices, such as, for example, wearable devices, wireless communication device handsets, or integrated circuit devices for wearable devices, wireless communication device handsets, and other devices. Any features described as devices or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory, non-volatile random access memory (NVRAM), electrically erasable programmable read-only memory (EEPROM), flash memory, magnetic or optical data storage media, and the like. The techniques additionally, or alternatively, may be realized at least in part by a computer-readable communication medium that carries or communicates program code in the form of instructions or data structures and that can be accessed, read, and/or executed by a computer, such as propagated signals or waves.

According to some embodiments, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices, wearable devices, or any other device that incorporates hard-wired and/or program logic to implement the techniques.

Processor(s) in communication with (e.g., operating in collaboration with) the computer-readable medium (e.g., memory or other data storage device) may execute instructions of the program code, and may include one or more processors, such as one or more digital signal processors (DSPs), general purpose microprocessors, ASICs, FPGAs, or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices, for example, a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein. Also, the techniques could be fully implemented in one or more circuits or logic elements.

The techniques of this disclosure may be implemented in a wide variety of devices or apparatuses, including a wearable device, a wireless handset, an integrated circuit (IC) or a set of ICs (e.g., a chip set). Various components, or units are described in this disclosure to emphasize functional aspects of devices configured to perform the disclosed techniques, but do not necessarily require realization by different hardware units. Rather, as described above, various units may be combined in a hardware unit or provided by a collection of inter-operative hardware units, including one or more processors as described above, in conjunction with suitable software and/or firmware.

Although the foregoing has been described in connection with various different embodiments, features, or elements from one embodiment may be combined with other embodiments without departing from the teachings of this disclosure. However, the combinations of features between the respective embodiments are not necessarily limited thereto.

What is claimed is:

1. A computer-implemented method, comprising:
   determining a sleep period of a user using at least motion data of the user captured by one or more motion sensors;
   determining, for the sleep period of the user, breathing disturbance data based at least in part on a decrease in blood oxygenation reflected in photoplethysmographic (PPG) data captured by one or more PPG sensors of a wearable device configured to be worn by the user;

calculating a sleep fitness score for the user over the sleep period, based at least in part on by classifying a plurality of temporal windows within the sleep period as representing disturbed breathing for the user or not breathing disturbed for the user according to the breathing disturbance data;

adjusting a duration of each of the plurality of temporal windows based on a sleeping or breathing pattern of the user; and providing, for presentation on a display device, at least one of the sleep fitness score or the breathing disturbance data.

2. The computer-implemented method of claim 1, further comprising:

determining an amount of motion for the sleep period using the motion data captured by the one or more motion sensors;

calculating the sleep fitness score based at least in part upon a difference between the breathing disturbance data and historical baseline breathing disturbance data for the user, and the determined amount of motion for the sleep period.

3. The computer-implemented method of claim 1, further comprising:

capturing respiration rate data for the user over the sleep period using a bed sensor; and calculating the sleep fitness score further based upon the respiration rate data for the user.

4. The computer-implemented method of claim 1, further comprising:

updating a baseline breathing score for the user using the breathing disturbance data; and providing, for presentation on the display device, the updated baseline breathing score.

5. The computer-implemented method of claim 1, wherein the PPG data is captured using a green light PPG sensor, a red light PPG sensor, and an infrared PPG sensor.

6. The computer-implemented of claim 1, further comprising:

determining a percentage of temporal windows, out of the plurality of temporal windows for the sleep period, classified as representing disturbed breathing for the user; and generating the sleep fitness score based at least on the percentage of temporal windows.

7. The computer-implemented of claim 6, further comprising:

generating additional sensor data by at least one additional sensor, during a second period outside the sleep period;

determining a baseline physiological metric associated with the user based on the additional sensor data; and classifying respective temporal windows based at least upon the baseline physiological metric associated with the user.

8. A computer-implemented method, comprising:

capturing, by a plurality of sensors, breathing pattern data and motion data of a user;

receiving, by one or more processors, the breathing pattern data and the motion data captured by the plurality of sensors;

determining, by the one or more processors using the motion data, a sleep period for the user;

analyzing, by the one or more processors, the breathing pattern data captured during the sleep period, to determine sleep disturbances during the sleep period, the sleep disturbances determined based at least on the breathing pattern data captured during the sleep period and the sleep period, wherein the breathing pattern data indicates a decrease in blood oxygenation reflected in photoplethysmographic (PPG) data captured by one or more PPG sensors of a wearable device configured to be worn by the user;

classifying, by the one or more processors, a plurality of temporal windows during the sleep period as representing disturbed breathing for the user or not breathing disturbed for the user based on at least the breathing pattern data;

adjusting a duration of each of the plurality of temporal windows based on a sleeping or breathing pattern of the user;

calculating a sleep fitness score based at least on the sleep disturbances during the sleep period and the classification of the plurality of temporal windows during the sleep period; and displaying the sleep fitness score.

9. The computer-implemented method of claim 8, further comprising:

determining the sleep period in part based on at least a threshold period of time in which an amount of motion represented by the motion data is less than a motion threshold.

10. The computer-implemented method of claim 8, further comprising:

calculating breathing disturbance data using the breathing pattern data.

11. The computer-implemented method of claim 10, further comprising:

calculating the sleep fitness score based further upon the breathing disturbance data and the motion data.

12. The computer-implemented method of claim 8, further comprising:

calculating the sleep fitness score further based upon respiration rate data captured for the user over the sleep period.

13. The computer-implemented method of claim 10, wherein displaying the sleep fitness score comprises displaying the sleep fitness score on the wearable device.

14. A system, comprising:

at least one processor; and non-transitory computer-readable memory including instructions that, when executed by the at least one processor, cause the system to:

determine a sleep period of a user using at least motion data of the user captured by one or more motion sensors;

determine, for the sleep period of the user, breathing disturbance data based at least in part on a decrease in blood oxygenation reflected in captured photoplethysmographic (PPG) data captured by one or more PPG sensors of a wearable device configured to be worn by the user;

calculate a sleep fitness score for the user over the sleep period based at least in part on by classifying a plurality of temporal windows within the sleep period as representing disturbed breathing for the user or not breathing disturbed for the user according to the breathing disturbance data;

adjusting a duration of each of the plurality of temporal windows based on a sleeping or breathing pattern of the user; and provide, for presentation on a display device, at least one of the sleep fitness score or the breathing disturbance data.

15. The system of claim 14, wherein the instructions when executed further cause the system to:
determine the sleep period in part based on at least a threshold period of time in which an amount of motion represented by the motion data is less than a motion threshold.

16. The system of claim 14, wherein
the one or more PPG sensors include a red-light PPG sensor and an infrared PPG sensor, and
the instructions when executed further cause the system, for each temporal window among the plurality of temporal windows, to:
classify the temporal window as representing disturbed breathing for the user when a direct current (DC) signal of sensor data from the red-light PPG sensor divided by a DC signal of sensor data from the infrared PPG sensor maintains a value between a low threshold value and a high threshold value for a first threshold duration of time,
classify the temporal window using a motion-insensitive component of each of the red-light PPG sensor and the infrared PPG sensor,
classify the temporal window using a tissue oxygenation component of each of the sensor data from the red-light PPG sensor and the infrared PPG sensor, and
classify the temporal window as representing disturbed breathing for the user when detecting a pattern of respiration below a threshold level of respiration over a second threshold duration of time.

17. The system of claim 14, wherein the instructions when executed further cause the system to:
calculate the sleep fitness score based further upon the motion data.

18. The system of claim 14, wherein the instructions when executed further cause the system to:
calculate the sleep fitness score further based upon respiration rate data captured for the user over the sleep period.

19. The system of claim 14, further comprising the wearable device configured to be worn on a wrist of the user.

20. The system of claim 14, wherein the instructions when executed further cause the system to:
extract a low-frequency component of first sensor data, generated by a red light PPG sensor, and a low-frequency component of second sensor data, generated by an infrared PPG sensor;
determine processed sensor data based on dividing the low-frequency component of the first sensor data by the low-frequency component of the second sensor data; and
classifying at least one of the plurality of temporal windows within the sleep period using the processed sensor data.

* * * * *